(12) United States Patent
Ksondzyk et al.

(10) Patent No.: US 9,542,042 B2
(45) Date of Patent: *Jan. 10, 2017

(54) SCANNING A SINGLE-LAYER CAPACITIVE SENSE ARRAY

(71) Applicant: Parade Technologies, Ltd., Santa Clara, CA (US)

(72) Inventors: Petro Ksondzyk, Seattle, WA (US); Vasyl Mandziy, Lviv (UA); Igor Kolych, Lviv (UA); Massoud Badaye, Sunnyvale, CA (US)

(73) Assignee: PARADE TECHNOLOGIES, LTD., Santa Clara, CA (US)

(*) Notice: Subject to any disclaimer, the term of this patent is extended or adjusted under 35 U.S.C. 154(b) by 169 days.

This patent is subject to a terminal disclaimer.

(21) Appl. No.: 14/514,654

(22) Filed: Oct. 15, 2014

(65) Prior Publication Data
US 2015/0062093 A1    Mar. 5, 2015

Related U.S. Application Data

(63) Continuation of application No. 14/038,423, filed on Sep. 26, 2013, now Pat. No. 8,866,491, which is a
(Continued)

(51) Int. Cl.
G01R 35/00 (2006.01)
G01R 27/26 (2006.01)
(Continued)

(52) U.S. Cl.
CPC ............ *G06F 3/0418* (2013.01); *G01N 27/22* (2013.01); *G01R 35/005* (2013.01); *G06F 3/044* (2013.01)

(58) Field of Classification Search
CPC ...... G06F 3/0418; G01N 27/22; G01R 35/005
(Continued)

(56) References Cited

U.S. PATENT DOCUMENTS 4,233,522 A    11/1980   Grummer et al.
4,686,332 A    8/1987    Greanias
(Continued)

FOREIGN PATENT DOCUMENTS

JP    2010205177 A    9/2010
WO   WO2010117882 A   10/2010
(Continued)

OTHER PUBLICATIONS

Fischer, Dirk, "Capacitive Touch Sensors: Application Fields, Technology Overview, and Implementation Example", Fujitsu Microelectronics Europe; Langen, Germany; v4, dated Jan. 12, 2010; 12 pages.
(Continued)

*Primary Examiner* — Amy He
(74) *Attorney, Agent, or Firm* — Morgan, Lewis & Bockius LLP

(57) ABSTRACT

A method performs a scan operation for a single-layer sensor array that includes transmit (TX) electrodes and receive (RX) electrodes. The method includes determining whether to include a signal value for an RX electrode in a computation of a slope parameter value for a TX electrode. The method computes an index sum based on an index of the RX electrode when the signal value for the RX electrode is included in the computation of the slope parameter value for the TX electrode. The method computes a signal sum based on the signal value for the RX electrode when the signal value for the RX electrode is included in the computation of the slope parameter value for the TX electrode. The method then computes the slope parameter value for the TX electrode based on the signal sum and the index sum.

20 Claims, 16 Drawing Sheets

Related U.S. Application Data continuation-in-part of application No. 13/800,468, filed on Mar. 13, 2013, now Pat. No. 8,866,490, and a continuation-in-part of application No. 13/405,071, filed on Feb. 24, 2012.

(60) Provisional application No. 61/785,131, filed on Mar. 14, 2013, provisional application No. 61/754,028, filed on Jan. 18, 2013, provisional application No. 61/559,590, filed on Nov. 14, 2011, provisional application No. 61/446,178, filed on Feb. 24, 2011.

(51) Int. Cl.
  *G06F 3/041* (2006.01)
  *G01N 27/22* (2006.01)
  *G06F 3/044* (2006.01)

(58) Field of Classification Search
  USPC .............. 324/601, 663, 687; 345/173, 174
  See application file for complete search history.

(56) References Cited

U.S. PATENT DOCUMENTS

| | | |
|---|---|---|
| 4,707,845 A | 11/1987 | Krein et al. |
| 5,834,845 A | 11/1998 | Stolmeijer |
| 7,129,935 B2 | 10/2006 | Mackey |
| 7,202,855 B2 | 4/2007 | Shigetaka et al. |
| 7,202,859 B1 | 4/2007 | Speck et al. |
| 7,265,809 B2 | 9/2007 | Dunn et al. |
| 7,280,173 B2 | 10/2007 | Kamijo |
| 7,382,139 B2 | 6/2008 | Mackey |
| 7,423,635 B2 | 9/2008 | Taylor et al. |
| 7,439,962 B2 | 10/2008 | Reynolds et al. |
| 7,499,039 B2 | 3/2009 | Roberts |
| 7,548,073 B2 | 6/2009 | Mackey |
| 7,821,425 B2 | 10/2010 | Philipp |
| 7,875,814 B2 | 1/2011 | Chen |
| 7,973,771 B2 | 7/2011 | Geaghan |
| 8,243,027 B2 | 8/2012 | Hotelling et al. |
| 8,274,488 B2 | 9/2012 | Bae |
| 8,294,687 B1 | 10/2012 | Ksondzyk |
| 8,300,019 B2 | 10/2012 | Elias et al. |
| 8,497,786 B2 | 7/2013 | Camacho |
| 8,508,680 B2 | 8/2013 | Geaghan et al. |
| 8,599,150 B2 | 12/2013 | Philpp |
| 8,866,490 B1 | 10/2014 | Mandziy et al. |
| 8,866,491 B2 | 10/2014 | Ksondzyk et al. |
| 9,256,327 B2 | 2/2016 | Salaverry |
| 2003/0210235 A1 | 11/2003 | Roberts |
| 2004/0175257 A1 | 9/2004 | Pallas |
| 2004/0239650 A1 | 12/2004 | Mackey |
| 2005/0270039 A1 | 12/2005 | Mackey |
| 2005/0270273 A1 | 12/2005 | Marten |
| 2006/0097991 A1 | 5/2006 | Hotelling et al. |
| 2006/0227115 A1 | 10/2006 | Fry |
| 2007/0008299 A1 | 1/2007 | Hristov |
| 2007/0074913 A1 | 4/2007 | Geaghan et al. |
| 2007/0132386 A1 | 6/2007 | Kim et al. |
| 2007/0257894 A1 | 11/2007 | Philipp |
| 2007/0279395 A1 | 12/2007 | Philipp et al. |
| 2008/0143683 A1 | 6/2008 | Hotelling |
| 2008/0158181 A1 | 7/2008 | Hamblin et al. |
| 2008/0246496 A1 | 10/2008 | Hristov et al. |
| 2008/0264699 A1 | 10/2008 | Chang et al. |
| 2009/0002337 A1 | 1/2009 | Chang |
| 2009/0090694 A1 | 4/2009 | Hotelling et al. |
| 2009/0159344 A1 | 6/2009 | Hotelling et al. |
| 2009/0273577 A1 | 11/2009 | Chen et al. |
| 2009/0314621 A1 | 12/2009 | Hotelling |
| 2010/0013800 A1 | 1/2010 | Elias et al. |
| 2010/0045614 A1 | 2/2010 | Gray et al. |
| 2010/0059294 A1 | 3/2010 | Elias et al. |
| 2010/0079401 A1 | 4/2010 | Staton |
| 2010/0090979 A1 | 4/2010 | Bae |
| 2010/0108409 A1 | 5/2010 | Tanaka et al. |
| 2010/0144391 A1 | 6/2010 | Chang et al. |
| 2010/0214260 A1 | 8/2010 | Tanaka et al. |
| 2010/0220071 A1 | 9/2010 | Nishihara et al. |
| 2010/0258360 A1 | 10/2010 | Yilmaz |
| 2010/0289774 A1 | 11/2010 | Pan et al. |
| 2010/0321326 A1 | 12/2010 | Grunthaner et al. |
| 2010/0321331 A1 | 12/2010 | Oda et al. |
| 2011/0012845 A1 | 1/2011 | Rothkopf et al. |
| 2011/0018841 A1 | 1/2011 | Hristov |
| 2011/0048812 A1 | 3/2011 | Yilmaz |
| 2011/0048813 A1 | 3/2011 | Yilmaz |
| 2011/0102361 A1 | 5/2011 | Philipp |
| 2011/0134070 A1 | 6/2011 | Wang et al. |
| 2011/0134075 A1 | 6/2011 | Takusa |
| 2011/0148785 A1 | 6/2011 | Oda et al. |
| 2011/0170099 A1 | 7/2011 | Ko |
| 2012/0050180 A1 | 3/2012 | King et al. |
| 2012/0081324 A1 | 4/2012 | Philipp |
| 2012/0098783 A1 | 4/2012 | Badaye et al. |
| 2012/0162090 A1 | 6/2012 | Chang et al. |
| 2012/0162144 A1 | 6/2012 | Faahraeus et al. |
| 2012/0182251 A1 | 7/2012 | Krah |
| 2012/0200530 A1 | 8/2012 | Wu et al. |
| 2012/0255167 A1 | 10/2012 | Badaye et al. |
| 2012/0256851 A1 | 10/2012 | Wang et al. |
| 2012/0262412 A1 | 10/2012 | Guard et al. |
| 2013/0021296 A1 | 1/2013 | Min et al. |
| 2013/0050105 A1 | 2/2013 | Lee et al. |
| 2013/0069905 A1 | 3/2013 | Krah et al. |
| 2013/0100054 A1 | 4/2013 | Philipp |
| 2013/0127772 A1 | 5/2013 | Guard et al. |
| 2013/0127775 A1 | 5/2013 | Yilmaz et al. |
| 2013/0181943 A1 | 7/2013 | Bulea et al. |
| 2013/0187704 A1 | 7/2013 | Edwards |
| 2013/0207911 A1 | 8/2013 | Barton et al. |
| 2013/0234974 A1 | 9/2013 | Guard |
| 2013/0329347 A1 | 12/2013 | Kuo |
| 2014/0092036 A1 | 4/2014 | Lin et al. |
| 2014/0192027 A1 | 7/2014 | Ksondzyk et al. |
| 2014/0210784 A1 | 7/2014 | Gourevitch et al. |

FOREIGN PATENT DOCUMENTS

| | | |
|---|---|---|
| WO | WO2010016174 A | 11/2010 |
| WO | WO2011/122782 A2 | 10/2011 |
| WO | 2012176639 A | 12/2012 |
| WO | WO2013179042 A | 12/2013 |

OTHER PUBLICATIONS

International Search Report for International Application No. PCT/US13/62331 dated Feb. 12, 2014; 2 pages.

USPTO Advisory Action for U.S. Appl. No. 13/800,468 dated Jul. 29, 2014; 2 pages.

USPTO Advisory Action for U.S. Appl. No. 14/038,423 dated Jul. 25, 2014; 2 pages.

USPTO Final Rejection for U.S. Appl. No. 13/800,468 dated May 22, 2014; 10 pages.

USPTO Final Rejection for U.S. Appl. No. 14/038,423 dated May 22, 2014; 11 pages.

USPTO Non-Final Rejection for U.S. Appl. No. 13/800,468 dated Jan. 21, 2014; 8 pages.

USPTO Non-Final Rejection for U.S. Appl. No. 14/038,423 dated Jan. 14, 2014; 9 pages.

USPTO Notice of Allowance for U.S. Appl. No. 13/800,468 dated Sep. 12, 2014; 8 pages.

USPTO Notice of Allowance for U.S. Appl. No. 14/038,423 dated Sep. 9, 2014; 9 pages.

Written Opinion of the International Searching Authority for International Application No. PCT/US13/ 62331 dated Feb. 12, 2014; 4 pages.

Wu, Xiaoling et al., "Touchware: A Software-Based Technique for High-Resolution Multi-Touch Sensing Devices," Int. J. Ad Hoc and Ubiquitous Computing, vol. X, No. X, 200x; 13 pages.

(56) References Cited

OTHER PUBLICATIONS

U.S. Appl. No. 13/248,776, "Single Layer Touch Sensor," Massoud Badaye, filed Sep. 29, 2011, 36 pgs.
U.S. Appl. No. 13/405,071, "Single Layer Touch Sensor," Massoud Badaye, filed Feb. 24, 2012, 64 pgs.
U.S. Appl. No. 13/800,468, "Method and Apparatus for Eliminating Tail Effect in Touch Applications," Vasyl Mandziy, filed Mar. 13, 2013, 51 pgs.
U.S. Appl. No. 61/446,178, "Single-Layer Multi-Touch Sensor," Matt Badaye, filed Feb. 24, 2011, 6 pgs.
U.S. Appl. No. 61/559,590, "Single Layer Touch Sensor," Massoud Badaye, filed Nov. 14, 2011, 35 pgs.
U.S. Appl. No. 61/607,513, "Single Layer Multi-Touch Sensor," Matt Badaye, filed Mar. 6, 2012, 11 pgs.
Application No. PCT/US2011/053916, "Single Layer Touch Sensor," filed on Sep. 29, 2011, 35 pgs.
Badaye, Office Action, U.S. Appl. No. 13/405,071, Jul. 21, 2014, 16 pgs.
Badaye, Final Office Action, U.S. Appl. No. 13/405,071, Oct. 16, 2014, 22 pgs.
Badaye, Final Office Action, U.S. Appl. No. 13/405,071, Jul. 22, 2015, 21 pgs.
Badaye, Office Action, U.S. Appl. No. 13/405,071, Apr. 7, 2016, 15 pgs.
Badaye, Office Action, U.S. Appl. No. 13/528,739, Apr. 29, 2015, 19 pgs.
Badaye, Final Office Action, U.S. Appl. No. 13/528,739, Dec. 15, 2015, 19 pgs.
Gourevitch, Office Action, U.S. Appl. No. 14/229,524, Jul. 29, 2014, 15 pgs.
Gourevitch, Final Office Action, U.S. Appl. No. 14/229,524, Oct. 23, 2014, 16 pgs.
Gourevitch, Office Action, U.S. Appl. No. 14/229,524, May 28, 2015, 16 pgs.
Gourevitch, Final Office Action, U.S. Appl. No. 14/229,524, Jan. 14, 2016, 16 pgs.
International Search Report and Written Opinion, PCT/US2011/053916, dated Apr. 10, 2012, 8 pgs.
International Search Report and Written Opinion, PCT/US2012/026634, dated May 29, 2012, 7 pgs.
Kravets, Office Action, U.S. Appl. No. 14/318,354, Sep. 9, 2014, 18 pgs.
Kravets, Final Office Action, U.S. Appl. No. 14/318,354, Dec. 26, 2014, 19 pgs.
Kravets, Office Action, U.S. Appl. No. 14/318,354, Jun. 10, 2015, 19 pgs.
Kravets, Final Office Action, U.S. Appl. No. 14/318,354, Dec. 15, 2015, 21 pgs.
Kravets, Notice of Allowance, U.S. Appl. No. 14/318,354, Mar. 16, 2016, 10 pgs.
Prendergast, Office Action, U.S. Appl. No. 14/666,764, Apr. 15, 2016, 14 pgs.
USPTO, Office Action, U.S. Appl. No. 13/528,644, dated Nov. 20, 2012, 6 pgs.
USPTO, Notice of Allowance, U.S. Appl. No. 13/528,644, dated Jan. 25, 2013, 5 pgs.
USPTO, Notice of Allowance, U.S. Appl. No. 13/528,644, dated Apr. 23, 2013, 6 pgs.
USPTO, Notice of Allowance, U.S. Appl. No. 13/528,644, dated Jun. 7, 2013, 6 pgs.
International Search Report and Written Opinion, PCT/US2014/051363, dated Dec. 18, 2014, 9 pgs.
Badaye, Final Office Action, U.S. Appl. No. 13/405,071, Aug. 17, 2016, 19 pgs.
Prendergast, Final Office Action, U.S. Appl. No. 14/666,764, Aug. 16, 2016, 18 pgs.

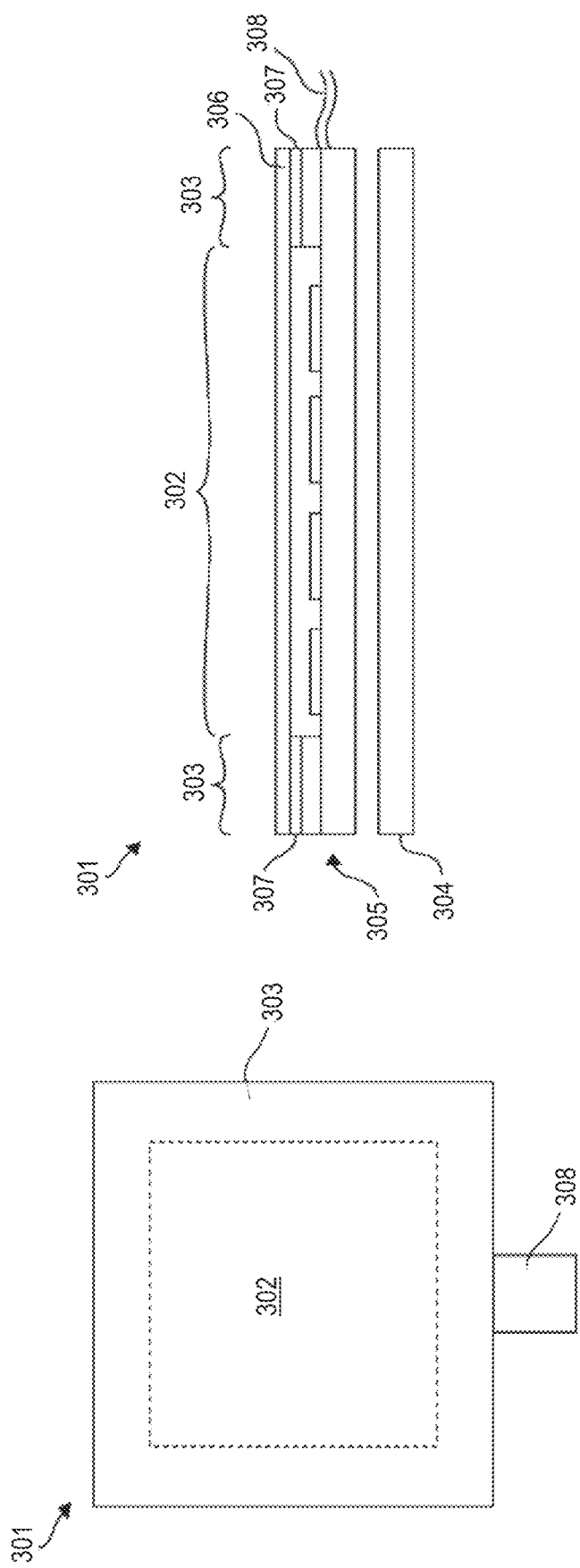

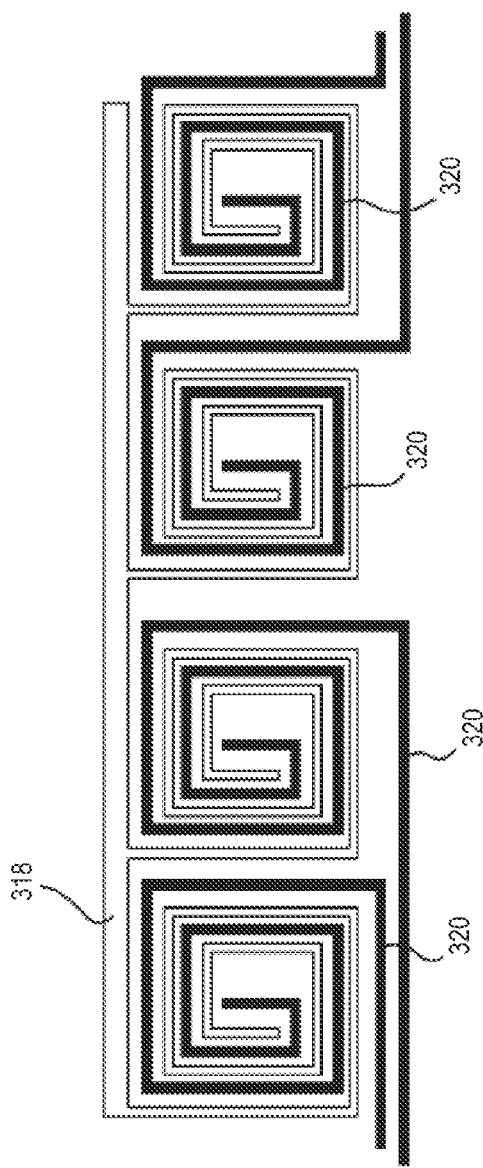
FIG. 4A
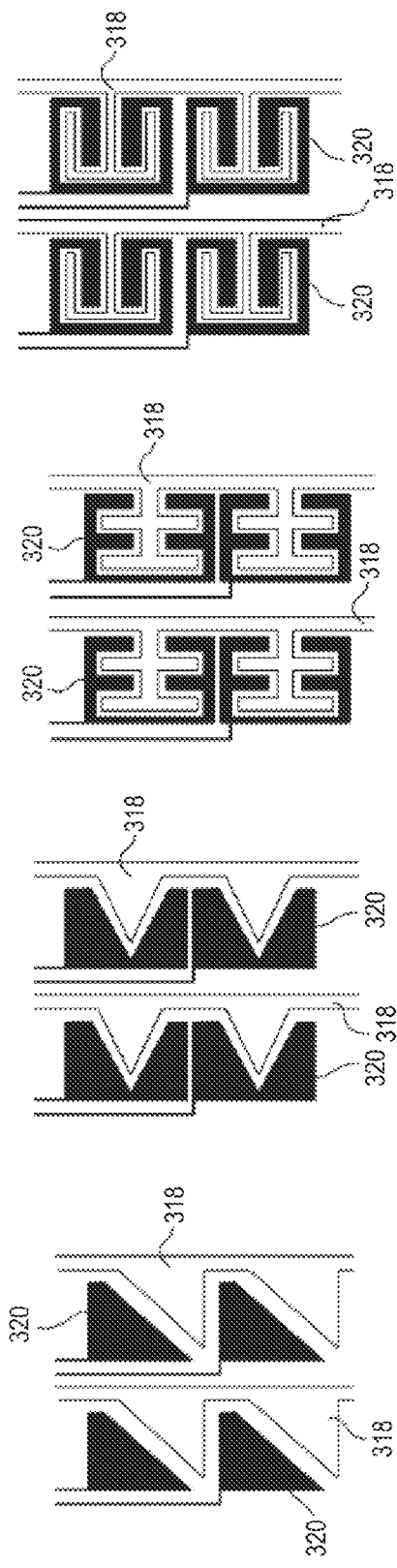
FIG. 4E
FIG. 4D
FIG. 4C
FIG. 4B

702 TX Index

| | 0 | 1 | 2 | 3 | 4 | 5 | 6 | 7 | 8 | 9 | 10 |
|---|---|---|---|---|---|---|---|---|---|---|---|
| 0 | 1 | 1 | -3 | 5 | 47 | 48 | 45 | 5 | 1 | 0 | 2 |
| 1 | -1 | -2 | 17 | 125 | 165 | 169 | 165 | 127 | 12 | 0 | 0 |
| 2 | -3 | -7 | 47 | 179 | 170 | 167 | 166 | 168 | 33 | -2 | 1 |
| 3 | -3 | -3 | 7 | 110 | 171 | 190 | 186 | 122 | 8 | -2 | -5 |
| 4 | -4 | -5 | 5 | 21 | 42 | 71 | 57 | 30 | 9 | -2 | -3 |
| 5 | -4 | -3 | 2 | 15 | 25 | 28 | 34 | 22 | 3 | -2 | -2 |
| 6 | -2 | -4 | 3 | 12 | 30 | 19 | 27 | 11 | 1 | -1 | -4 |
| 7 | -4 | -3 | 4 | 16 | 26 | 33 | 26 | 14 | -1 | -1 | -3 |
| 8 | -4 | -3 | 10 | 25 | 34 | 39 | 31 | 13 | 0 | -2 | -6 |
| 9 | -2 | 0 | 13 | 34 | 32 | 37 | 38 | 21 | 0 | -1 | -3 |
| 10 | 1 | 0 | -7 | -5 | 0 | -2 | 0 | -4 | -3 | -1 | 3 |
| 11 | 2 | 0 | -3 | -1 | -1 | -1 | 0 | -2 | -2 | -1 | 1 |
| 12 | 0 | 0 | -1 | -1 | 0 | -1 | -1 | 0 | 0 | 0 | 1 |
| 13 | 0 | 0 | -1 | -2 | 0 | 0 | -1 | 0 | 0 | 0 | 0 |
| 14 | 0 | 0 | 0 | -1 | 0 | -1 | -1 | -1 | -1 | 0 | 0 |
| 15 | 0 | 0 | -2 | -2 | 0 | -1 | 0 | 0 | -1 | 1 | 0 |
| 16 | 1 | 0 | 0 | -2 | 0 | -1 | 0 | -1 | 0 | 1 | 0 |
| 17 | 0 | 0 | -1 | -3 | -1 | -1 | -1 | -1 | 0 | 0 | 0 |
| 18 | 1 | 1 | 0 | -1 | -1 | 0 | -2 | -2 | 0 | 0 | 1 |

704 RX Index 706b contact
708b tail effect
701b diff signal value
700

FIG. 7B

1002 TX Index

| | 0 | 1 | 2 | 3 | 4 | 5 | 6 | 7 | 8 | 9 | 10 |
|---|---|---|---|---|---|---|---|---|---|---|---|
| 0 | 0 | 0 | -2 | 0 | 0 | 0 | 0 | 0 | 0 | 0 | 0 |
| 1 | 0 | 0 | 0 | 0 | 0 | 0 | 0 | 0 | 0 | 0 | 0 |
| 2 | 0 | 0 | 0 | 0 | 0 | 0 | 0 | -1 | 0 | 0 | 0 |
| 3 | 0 | 0 | 0 | 0 | 0 | 0 | 0 | 0 | 0 | 0 | 0 |
| 4 | 0 | 0 | -1 | 0 | 0 | 0 | 0 | 0 | 0 | 0 | 0 |
| 5 | 0 | 0 | 0 | 0 | 0 | 0 | 0 | 0 | 0 | 0 | 0 |
| 6 | 0 | 0 | 0 | 0 | 0 | 0 | 0 | 0 | 0 | 0 | 0 |
| 7 | -3 | -2 | 1 | 0 | 0 | 0 | 0 | 0 | -3 | -3 | 0 |
| 8 | -2 | -1 | 6 | 7 | 5 | 8 | 4 | 3 | -2 | -2 | 0 |
| 9 | -2 | -3 | 1 | 15 | 13 | 10 | 10 | 8 | -2 | 0 | 0 |
| 10 | -1 | 2 | 25 | 39 | 44 | 44 | 38 | 24 | 14 | 1 | 1 |
| 11 | 2 | 2 | 22 | 36 | 35 | 34 | 25 | 18 | 6 | 2 | 1 |
| 12 | 1 | 1 | 19 | 30 | 36 | 37 | 34 | 21 | 11 | 1 | 0 |
| 13 | 1 | 2 | 19 | 24 | 28 | 23 | 23 | 19 | 5 | 4 | -1 |
| 14 | 1 | 1 | 23 | 40 | 55 | 39 | 29 | 17 | 9 | 2 | 0 |
| 15 | 1 | 4 | 43 | 181 | 195 | 166 | 92 | -2 | 2 | 1 | 0 |
| 16 | 2 | 7 | 93 | 187 | 187 | 198 | 205 | 118 | 13 | 0 | 1 |
| 17 | 0 | 2 | 49 | 172 | 170 | 178 | 187 | 193 | 11 | -1 | -1 |
| 18 | -2 | 0 | -7 | 27 | 132 | 139 | 146 | 161 | 31 | 2 | -1 |

1008 tail effect 1006a contact

1004 RX Index

1002 TX Index

| | 0 | 1 | 2 | 3 | 4 | 5 | 6 | 7 | 8 | 9 | 10 |
|---|---|---|---|---|---|---|---|---|---|---|---|
| 0 | 0 | 0 | 0 | 0 | 0 | 0 | 0 | 0 | 0 | 0 | 0 |
| 1 | 0 | 0 | 0 | 0 | 0 | 0 | 0 | 0 | 0 | 0 | 0 |
| 2 | 0 | 0 | 0 | 0 | 0 | 0 | 0 | 0 | 0 | 0 | 0 |
| 3 | 0 | 0 | 0 | -1 | 0 | 0 | 0 | 0 | 0 | 0 | 0 |
| 4 | 0 | 0 | 0 | -1 | -1 | -1 | 0 | 0 | 0 | 0 | 0 |
| 5 | 0 | 0 | 0 | -2 | -1 | -1 | 0 | 0 | 0 | 0 | 0 |
| 6 | 0 | 0 | 0 | -2 | -1 | -1 | -1 | 0 | 0 | 0 | 0 |
| 7 | -3 | -2 | 1 | -5 | -1 | 0 | -1 | 0 | -3 | -4 | 0 |
| 8 | -1 | -1 | 3 | 2 | 1 | 3 | 1 | 0 | -2 | -2 | 0 |
| 9 | -3 | -3 | 0 | 8 | 7 | 5 | 5 | 4 | -2 | -2 | -1 |
| 10 | -4 | -1 | -23 | -7 | 0 | -4 | -1 | -1 | -6 | -1 | 0 |
| 11 | -1 | 0 | -19 | -4 | -2 | -6 | -7 | -3 | -9 | 1 | 2 |
| 12 | 0 | 0 | -18 | -4 | 3 | 1 | 4 | 1 | -2 | -1 | -1 |
| 13 | 0 | 0 | -10 | -3 | 0 | -5 | -1 | 3 | -6 | 2 | 0 |
| 14 | 1 | 1 | -3 | 21 | 47 | 17 | 8 | 2 | -3 | 1 | 0 |
| 15 | 1 | 2 | 17 | 161 | 181 | 155 | 86 | -11 | -5 | 1 | 0 |
| 16 | 2 | 2 | 48 | 181 | 164 | 178 | 194 | 121 | 3 | -3 | 0 |
| 17 | -1 | 0 | 12 | 146 | 163 | 173 | 181 | 192 | 7 | -2 | -2 |
| 18 | -2 | -2 | -5 | -2 | 109 | 141 | 147 | 163 | 25 | -1 | -2 |

1018 corrected tail 1006b contact

1004 RX Index

1000

FIG. 10B

SCANNING A SINGLE-LAYER CAPACITIVE SENSE ARRAY

PRIORITY

This application is a continuation of U.S. patent application Ser. No. 14/038,423, filed Sep. 26, 2013, which claims the priority and benefit of U.S. Provisional Application No. 61/785,131, filed on Mar. 14, 2013, both of which are incorporated by reference herein; U.S. patent application Ser. No. 14/038,423 is a continuation-in-part of U.S. patent application Ser. No. 13/800,468, filed on Mar. 13, 2013, which claims the priority and benefit of U.S. Provisional Application No. 61/754,028, filed on Jan. 18, 2013, both of which are incorporated by reference herein; U.S. patent application Ser. No. 14/038,423 is also a continuation-in-part of U.S. patent application Ser. No. 13/405,071, filed on Feb. 24, 2012, which claims the priority and benefit of U.S. Provisional Application No. 61/559,590, filed on Nov. 14, 2011, and the priority and benefit of U.S. Provisional Application No. 61/446,178, filed on Feb. 24, 2011, all of which are incorporated by reference herein.

TECHNICAL FIELD

This disclosure generally relates to the field of touch-sensor devices and, in particular, to processing of touch sensor data.

BACKGROUND

Computing devices, such as notebook computers, personal digital assistants, mobile communication devices, portable entertainment devices (e.g., handheld video games, multimedia players, etc.), and set-top-boxes (e.g., digital cable boxes, digital video disc (DVD) players, etc.) may include user interface devices that facilitate interaction between a user and the computing device. One type of user interface device that has become common is a touch-sensor device or touch input device that operates by way of capacitance sensing. A touch-sensor device may be embodied as a touchscreen, touch-sensor pad, touch-sensor slider, or touch-sensor buttons, and may include a touch sensor comprising an array of capacitive sensor elements. Capacitive sensing typically involves scan operations that periodically measure changes in capacitance associated with the capacitive sensor elements to determine a presence, position, and/or movement of a conductive object (e.g., a stylus, a user's finger, etc.) relative to the touch sensor.

Touch sensors are an expensive part of a touch-sensor device or the user interface system thereof. One reason for the high manufacturing cost of touch sensors is that conventional sensors use either multiple layers of electrode materials formed on multiple substrates or a single substrate with a series of "jumpers" to form electrical connection between the individual electrode segments and insulate them from the other electrodes that intersect them. One way to reduce the high cost of touch sensors is to route the trace portions (or segments) of electrodes tightly together on the active area of a single substrate without the use of "jumpers". However, this type of sensor construction leads to increased capacitive cross-coupling between the electrodes (e.g., especially in response to a conductive object touch), thereby causing false touches, inaccuracy, and poor touch-response linearity, all of which limit the functionality of the touch-sensor device and/or lead to poor user experience.

BRIEF DESCRIPTION OF THE DRAWINGS

FIG. 3A illustrates a simplified plan view of a touch-sensor device according to an example embodiment.

FIG. 3B illustrates a cross-sectional view of the touch-sensor device in FIG. 3A.

FIGS. 4A, 4B, 4C, 4D, and 4E illustrate alternative patterns of sensor electrodes on a single substrate layer according to various embodiments.

FIGS. 7A and 7B illustrate two example data structures storing signal values that reflect tail effects caused by conductive objects on each side of a double-routed touch sensor panel according to an example embodiment.

FIG. 10A illustrates a data structure storing measured signal values that reflect a tail effect caused by a conductive object on a double-routed touch sensor panel according to an example embodiment.

FIG. 10B illustrates a data structure storing signal values that are adjusted with a correction for the tail effect illustrated in FIG. 10A.

DETAILED DESCRIPTION

Figure 1:
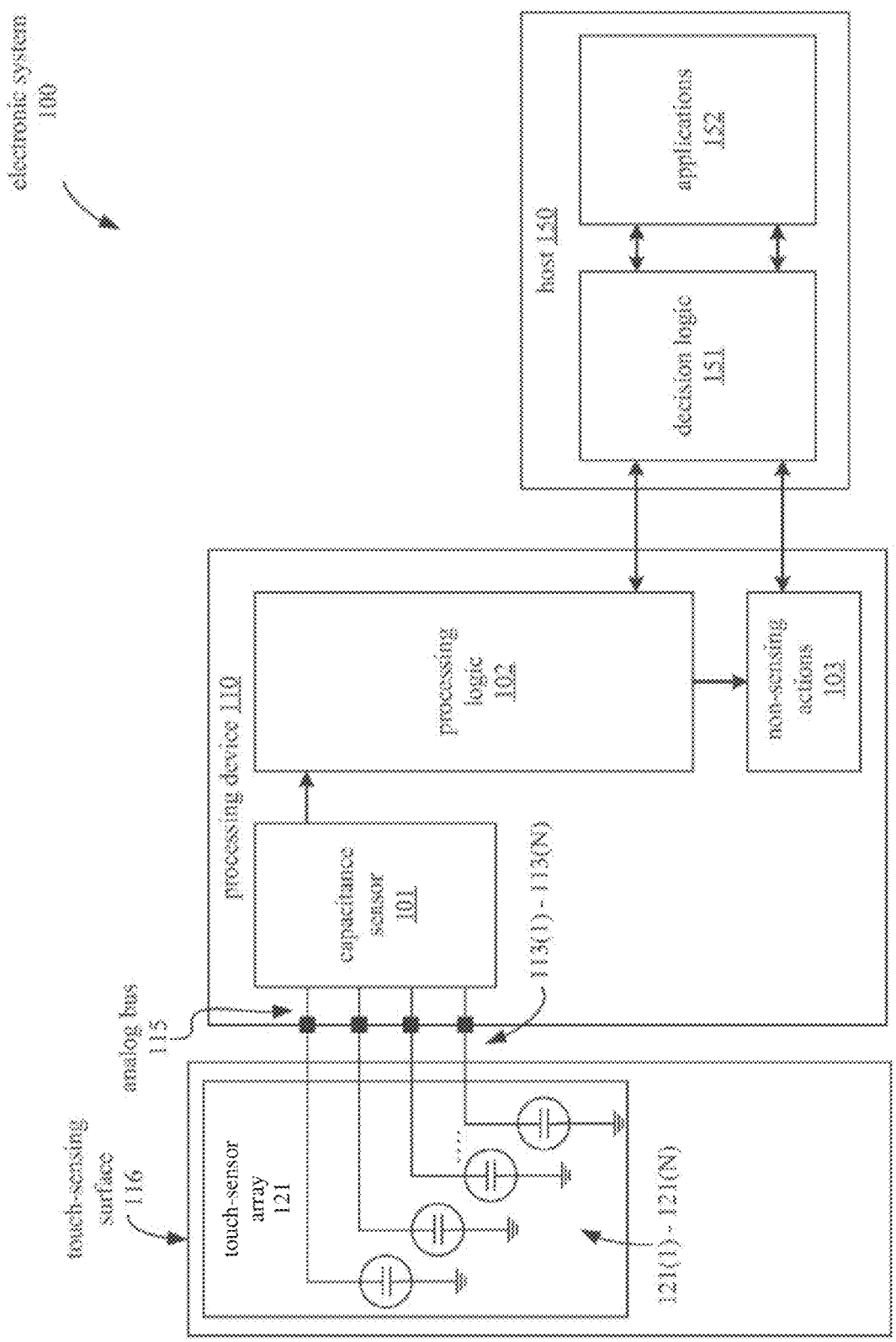
FIG. 1 is a block diagram illustrating an embodiment of an example electronic system that includes touch sensor components.

The following description sets forth numerous specific details such as examples of specific systems, components, methods, and so forth, in order to provide a good understanding of various embodiments of the techniques described herein for correcting tail effects in single-layer touch sensors (e.g., such as touch sensors with SLIM electrode patterns). It will be apparent to one skilled in the art, however, that at least some embodiments may be practiced without these specific details. In other instances, well-known components or methods are not described in detail or are presented in a simple block diagram format in order to avoid unnecessarily obscuring the techniques described herein. Thus, the specific details set forth hereinafter are merely exemplary. Particular implementations may vary from these exemplary details and still be contemplated to be within the spirit and scope of the present invention.

Reference in the description to "an embodiment", "one embodiment", "an example embodiment", "some embodiments", and "various embodiments" means that a particular feature, structure, or characteristic described in connection with the embodiment(s) is included in at least one embodiment of the invention. Further, the appearances of the phrases "an embodiment", "one embodiment", "an example embodiment", "some embodiments", and "various embodiments" in various places in the description do not necessarily all refer to the same embodiment(s).

The description includes references to the accompanying drawings, which form a part of the detailed description. The drawings show illustrations in accordance with exemplary embodiments. These embodiments, which may also be referred to herein as "examples," are described in enough detail to enable those skilled in the art to practice the embodiments of the claimed subject matter described herein. The embodiments may be combined, other embodiments may be utilized, or structural, logical, and electrical changes may be made without departing from the scope and spirit of the claimed subject matter. It should be understood that the embodiments described herein are not intended to limit the scope of the subject matter but rather to enable one skilled in the art to practice, make, and/or use the subject matter.

Overview

Described herein are various embodiments of techniques for correcting tail effects in a touch sensor with transmit (TX) and receive (RX) electrodes that are arranged in the same (e.g., single) layer of the substrate of the touch sensor. Unless expressly specified otherwise, "touch sensors" are also referred to herein as "sensor arrays", "touch sensor arrays", "touch panels", "touch sensor panels", and the like.

As used herein, "contact" refers to a physical touch of a conductive object (e.g., a stylus, a user's finger, and the like) on the touch-surface of a touch sensor and/or to a hover in which the conductive object is sufficiently proximate to affect the sensor elements of the touch sensor without being in physical touch with the touch-surface of the sensor. As used herein, "sensor element" refers to a discrete unit or location area (e.g., adjacency) of electrodes from which a measurement or signal can be obtained that is separate and distinct from measurements/signals obtained from other units or location areas in the touch sensor.

In single-layer touch sensors that use interleaved electrodes without "jumpers", a conductive object may affect portions (also referred to as "segments") from multiple electrodes, thereby causing a change in the capacitance even of electrodes that are not directly under the contact by conductive object and that should not register or otherwise detect the contact. Such parasitic signal coupling outside of the actual touch sensor area affected by the contact causes a parasitic signal increase or a parasitic signal decrease (e.g., depending on the type of sensing mechanism used by the touch sensor). Such parasitic signal increase or decrease in one or more sensor elements of a touch sensor is referred to herein as a "tail effect".

In one example embodiment, a device comprises a sensor coupled with a processing logic. The sensor is configured to measure a plurality of measurements from a sensor array during a scan operation, where the plurality of measurements is representative of a conductive object that is in contact with or proximate to the sensor array. The sensor array comprises a plurality of RX electrodes and a plurality of TX electrodes, where the plurality of RX electrodes and the plurality of TX electrodes are interleaved without intersecting each other in a single layer on a substrate of the sensor array. The processing logic is configured to determine a set of adjustment values that correspond to a tail effect associated with the plurality of measurements, and to generate adjusted measurements corresponding to the plurality of measurements based on the set of adjustment values, where the adjusted measurements correct a parasitic signal change of the tail effect. In some aspects of this embodiment, the tail effect comprises a parasitic signal increase or a parasitic signal decrease that is caused by parasitic coupling between a primary trace of a RX electrode and a TX electrode that are affected by the conductive object, where the primary trace of the RX electrode is routed adjacent to the TX electrode. The primary trace of the RX electrode and a shaped portion of the RX electrode are disposed in a touch-sensing area of the sensor array, but the shaped portion of the RX electrode is not affected by the conductive object.

In another example embodiment, a method for correcting tail effects comprises the steps of: receiving a plurality of measurements that are measured from a sensor array, where the plurality of measurements are representative of a conductive object that is in contact with or proximate to the sensor array, and where the sensor array comprises a plurality of RX electrodes and a plurality of TX electrodes that are interleaved without intersecting each other in a single layer on a substrate of the sensor array; a processing device determining a set of adjustment values that correspond to a tail effect associated with the plurality of measurements; and generating adjusted measurements corresponding to the plurality of measurements based on the set of adjustment values, where the adjusted measurements correct a parasitic signal change of the tail effect. In some aspects of this embodiment, the plurality of measurements include signal values for sensor elements formed by a particular TX electrode of the sensor array, and determining the adjusted measurements comprises the steps of: computing a sum of indices of RX electrodes that form the sensor elements along the particular TX electrode; computing a sum of the signal values for the sensor elements along the particular TX electrode; computing a parameter value based on the sum of indices and the sum of the signal values; and adjusting each signal value of the signal values, to obtain a corresponding adjusted value, based at least on: said each signal value, the parameter value, and an index of a corresponding RX electrode.

In another example embodiment, a system comprises a capacitive sensor array coupled with a capacitive sensor and a processing logic coupled with the capacitive sensor. The capacitive sensor array comprises a plurality of RX electrodes and a plurality of TX electrodes, where the plurality of RX electrodes and the plurality of TX electrodes are interleaved without intersecting each other in a single layer on a substrate of the capacitive sensor array. The capacitive sensor is configured to measure a plurality of measurements from the plurality of RX electrodes, where the plurality of measurements is representative of a conductive object that is in contact with or proximate to the capacitive sensor array. The processing logic is configured to determine a set of adjustment values that correspond to a tail effect associated with the plurality of measurements, and to generate adjusted measurements corresponding to the plurality of measurements based on the set of adjustment values, where the adjusted measurements correct a parasitic signal change of the tail effect.

Example Operational Contexts

FIG. 1 illustrates a block diagram of one example embodiment of an electronic system 100 including a processing device 110 that may be configured to measure capacitances from a touch-sensing surface and to generate adjustments to compensate for, and/or eliminate, tail effects. The electronic system 100 includes a touch-sensing surface 116 (e.g., a touchscreen, a touch pad, or the like) coupled to the processing device 110 and a host 150. In some embodiments, the touch-sensing surface 116 is a user interface that uses a touch sensor array 121 to detect touches on the surface 116.

In the example embodiment of FIG. 1, the touch sensor 121 includes sensor electrodes 121(1)-121(N) (where N is a positive integer) that are interleaved without intersecting each other (e.g., in a SLIM pattern) on a single layer of a substrate. The touch sensor 121 is coupled to pins 113(1)-113(N) of the processing device 110 via one or more analog buses 115 transporting multiple signals. For illustration purposes, in this embodiment each electrode 121(1)-121(N) is represented as a capacitor. The self-capacitance of each electrode in touch sensor 121 is measured by a capacitance sensor 101 in the processing device 110. Depending on the type of touch sensor, in some embodiments the capacitance sensor may be configured to detect the mutual capacitance of an electrode when a conductive object (e.g., stylus, user's finger, etc.) is in contact with one or more electrodes.

Capacitance sensor 101 (also referred to as just "sensor") may include a relaxation oscillator or other means to convert a capacitance into a measured value. Capacitance sensor 101 may also include a counter or timer to measure the oscillator output. The capacitance sensor 101 may further include software components to convert the count value (e.g., capacitance value) into a detection decision (also referred to as switch detection decision) or relative magnitude. In some embodiments, the measured value obtained by capacitance sensor 101 may be a signal value that represents one or more characteristics of a signal; in addition, or instead of, in some embodiments a signal value may be a value that is derived from the measured value based on a signal characteristic, e.g., such as voltage and/or current magnitude, raw capacitance, and the like. It should be noted that there are various known methods for measuring capacitance, such as current versus voltage phase shift measurement, resistor-capacitor charge timing, capacitive bridge divider, charge transfer, successive approximation, sigma-delta modulators, charge-accumulation circuits, field effect, mutual capacitance, frequency shift, or other capacitance measurement algorithms. It should also be noted that instead of evaluating the raw counts relative to a threshold, a capacitance sensor may be evaluating other measurements to determine the user interaction. For example, in a capacitance sensor having a sigma-delta modulator, the capacitance sensor may be evaluating the ratio of pulse widths of the output, instead of the raw counts being over or under a certain threshold.

In the example embodiment of FIG. 1, processing device 110 further includes processing logic 102. Operations of processing logic 102 may be implemented in firmware; alternatively, they may be implemented in hardware or software. Processing logic 102 is configured to perform operations that implement the techniques for correcting tail effects as described herein. For example, processing logic 102 may receive measurements from capacitance sensor 101, adjust the measurements to compensate/eliminate tail effects, and then use the adjusted measurements to determine the state of touch sensor 121, such as whether an object (e.g., a finger, a stylus, or the like) is detected on or in proximity to the touch sensor (e.g., determining the presence of the object), where the object is detected on the touch sensor (e.g., determining the location of the object), tracking the motion of the object, or other information related to an object detected at the touch sensor.

In another embodiment, instead of performing the operations of the processing logic in a processing device (e.g., such as processing device 110), the processing device may send the raw data or partially-processed data to a host, e.g., such as host 150. As illustrated in FIG. 1, host 150 may include decision logic 151 that performs some or all of the operations described above for processing logic 102. Operations of decision logic 151 may be implemented in firmware, hardware, software, or a combination thereof. Host 150 may include a high-level Application Programming Interface (API) in applications 152 that perform routines on the received data, such as compensating for sensitivity differences, other compensation algorithms, baseline update routines, start-up and/or initialization routines, interpolation operations, scaling operations and/or operations that implement the techniques for correcting tail effects as described herein. The operations described with respect to the processing logic 102 may be implemented in the decision logic 151, the applications 152, or in other hardware, software, and/or firmware external to the processing device 110. In some other embodiments, the processing device 110 may be the host 150.

In another embodiment, processing device 110 may also include a non-sensing actions block 103. This block 103 may be used to process and/or receive/transmit data to and from the host 150. For example, additional components may be implemented to operate with the processing device 110 along with touch sensor 121 (e.g., keyboard, keypad, mouse, trackball, LEDs, displays, or other peripheral devices).

Processing device 110 may reside on a common carrier substrate such as, for example, an integrated circuit (IC) die substrate, or a multi-chip module substrate. Alternatively, the components of the processing device 110 may be one or more separate integrated circuits and/or discrete components. In one embodiment, processing device 110 may be a programmable system on a chip that is manufactured on a single IC die such as, for example, the Programmable System on a Chip (PSoC™) processing device, developed by Cypress Semiconductor Corporation, San Jose, Calif. Alternatively, processing device 110 may be one or more other processing devices known by those of ordinary skill in the art, such as a microprocessor or central processing unit, a controller, a special-purpose processor, a digital signal processor (DSP), an application specific integrated circuit (ASIC), a field programmable gate array (FPGA), or other programmable device. In an alternative embodiment, for example, processing device 110 may be a network processor having multiple processors including a core unit and multiple micro-engines. Additionally, processing device 110 may include any combination of general-purpose processing device(s) and special-purpose processing device(s).

In one embodiment, electronic system 100 is implemented in a device that includes touch-sensing surface 116 as the user interface, such as handheld electronics, portable and/or smart telephones, cellular telephones, notebook computers, personal computers, personal data assistants (PDAs), kiosks, keyboards, televisions, remote controls, monitors, handheld multimedia devices, handheld video players, gaming devices, control panels of a household or industrial appliances, or other computer peripheral or input devices. Alternatively, electronic system 100 may be used in other types of devices. It should be noted that the components of electronic system 100 may include all the components described above. Alternatively, electronic system 100 may include only some of the components described above, or include additional components not listed herein.

Figure 2:
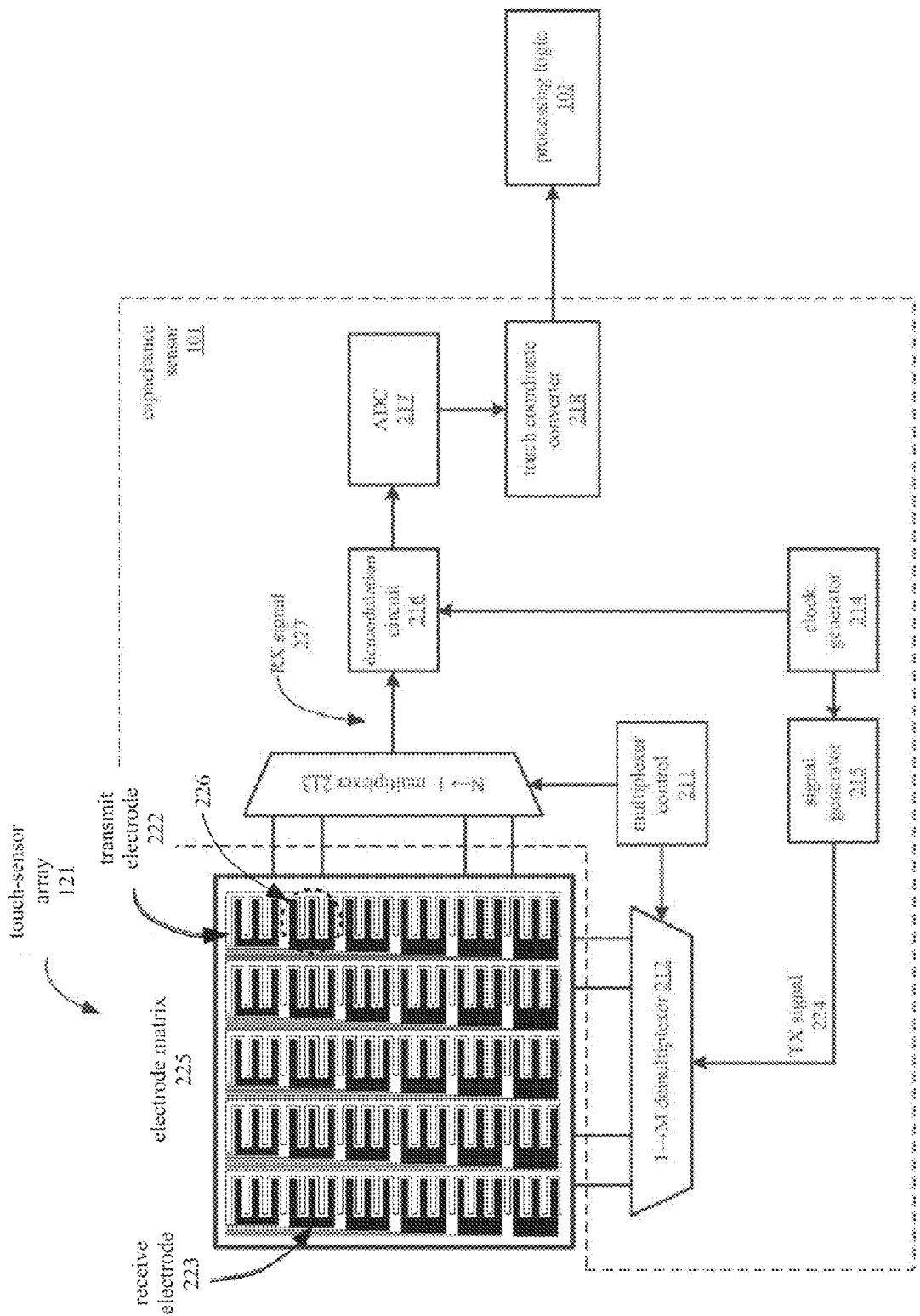
FIG. 2 is a block diagram illustrating an embodiment of an example sensor system that processes touch sensor data.

FIG. 2 is a block diagram illustrating one embodiment of a capacitive touch sensor array 121 (also referred to as "touch sensor") and a capacitance sensor 101 (also referred to as just "sensor") that converts measured capacitances to coordinates. The coordinates are calculated based on measured capacitances. In one embodiment, touch sensor 121 and capacitance sensor 101 are implemented in a system such as electronic system 100. Touch sensor 121 includes a matrix 225 having N receive electrodes and M transmit electrodes. For example, matrix 225 includes transmit (TX) electrode 222 and receive (RX) electrode 223. Each of the electrodes in matrix 225 is connected with capacitance sensing circuit 201 through demultiplexer 212 and multiplexer 213.

Capacitance sensor 101 includes multiplexer control 211, demultiplexer 212 and multiplexer 213, clock generator 214, signal generator 215, demodulation circuit 216, and analog to digital converter (ADC) 217. ADC 217 is further coupled with touch coordinate converter 218. Touch coordinate converter 218 outputs a signal to processing logic 102.

The transmit and receive electrodes in matrix 225 may be arranged so that each of the transmit electrodes is interleaved with the receive electrodes on the same (e.g., a single) substrate layer, but without intersecting the receive electrodes and while maintaining electrical (e.g., galvanic) isolation from them. Thus, each transmit electrode may be capacitively coupled with each of the receive electrodes. For example, transmit electrode 222 is capacitively coupled with receive electrode 223 at sensor-element area 226 of matrix 225, where the "E"-shaped portion of receive electrode 223 is interleaved with the "comb"-shaped portion of transmit electrode 222. In the electrode pattern illustrated in matrix 225, the "E"-shaped portions at the same horizontal level are electrically coupled to each other in the bezel portion (not shown) of touch sensor 121 to form a single (horizontal) receive electrode, while each transmit electrode is "comb"-shaped and runs (vertically) from the top to the bottom of matrix 225.

In some embodiments, a capacitance sensor (e.g., such as sensor 101 in FIG. 1) may be configured to use mutual capacitance sensing technique according to which a mutual capacitance present at the sensor-element area of two electrodes can be measured by a processing device (e.g., such as processing device 120 in FIG. 1). The change in this mutual capacitance at one or more sensor-element areas allows a processing logic to determine the location of a contact on the touch sensor. With mutual capacitance sensing, one set of electrodes (e.g., such as the column electrodes) are designated as transmit (TX) electrodes. The transmit electrodes are driven with a TX signal that is applied to the transmit electrodes by a transmit multiplexer. Another set of electrodes (e.g., such as the row electrodes) are designated as receive (RX) electrodes. The mutual capacitance of the sensor elements, formed at the areas where the rows and columns of electrodes are interleaved with each other, may be measured by sampling a signal on each of the receive electrodes. In some embodiments, a receive multiplexer may be used to sample the signal on one or more of the receive electrodes and to provide the receive measurement signal back to the processing logic 102 (and/or to another component of the processing device).

Referring back to FIG. 2, clock generator 214 supplies a clock signal to signal generator 215, which produces a transmit (TX) signal 224 to be supplied to the transmit electrodes of touch sensor 121. In one embodiment, signal generator 215 includes a set of switches that operate according to the clock signal from clock generator 214. The switches may generate a TX signal 224 by periodically connecting the output of signal generator 215 to a first voltage and then to a second voltage, where said first and second voltages are different.

The output of signal generator 215 is connected with demultiplexer 212, which allows a TX signal 224 to be applied to any of the M transmit electrodes of touch sensor 121. In one embodiment, multiplexer control 211 controls demultiplexer 212 so that the TX signal 224 is applied to each transmit electrode 222 in a controlled sequence. Demultiplexer 212 may also be used to ground, float, or connect an alternate signal to the other transmit electrodes to which the TX signal 224 is not currently being applied.

Because of the capacitive coupling between the transmit electrodes and the receive electrodes, a TX signal 224 applied to each transmit electrode induces a current within each of the receive electrodes. For instance, when the TX signal 224 is applied to transmit electrode 222 through demultiplexer 212, the TX signal 224 induces a receive (RX) signal 227 on the receive electrodes in matrix 225. The RX signal 227 on each of the receive electrodes can then be measured in sequence by using multiplexer 213 to connect each of the N receive electrodes to demodulation circuit 216 in sequence.

The mutual capacitance associated with each sensor element (e.g., the area where a given TX electrode is interleaved with a given an RX electrode), can be sensed by selecting every available combination of TX electrode and RX electrode using demultiplexer 212 and multiplexer 213. To improve performance, multiplexer 213 may also be segmented to allow more than one of the receive electrodes in matrix 225 to be routed to additional demodulation circuits 216. In an optimized configuration, where there is a 1-to-1 correspondence of instances of demodulation circuit 216 with receive electrodes, multiplexer 213 may not be present in the system.

When an object, such as a finger, approaches electrode matrix 225, the object causes a decrease in the mutual capacitance between only some of the electrodes. For example, if a finger is placed near sensor-element area 226 (where transmit electrode 222 is interleaved with receive electrode 223), the presence of the finger will decrease the mutual capacitance between electrodes 222 and 223. Thus, the location of the finger on touch sensor 121 can be determined by identifying the one or more receive electrodes having a decreased mutual capacitance and by identifying the transmit electrode to which the TX signal 224 was applied at the time the decreased mutual capacitance was measured on the one or more receive electrodes.

By determining the mutual capacitances associated with each sensor element formed by the transmit and receive electrodes in matrix 225, the locations of one or more touch contacts may be determined. The determination may be sequential, in parallel, or may occur more frequently at commonly used electrodes.

In some embodiments, other methods for detecting the presence of a finger or conductive object may be used where the finger or conductive object causes an increase in capacitance at one or more electrodes, which may be arranged in a particular interleaved pattern. For example, a finger placed near an electrode of a touch sensor may introduce an additional capacitance to ground that increases the total capacitance between the electrode and ground. The location of the finger can be determined from the locations of one or more electrodes at which an increased capacitance is detected.

The induced current signal 227 is rectified by demodulation circuit 216. The rectified current output by demodulation circuit 216 can then be filtered and converted to a digital code by ADC 217.

The digital code may then be converted to touch location coordinates indicating a position of an input on touch sensor 121 by touch coordinate converter 218. The touch location coordinates are transmitted as an input signal to processing logic 102. In one embodiment, the input signal is received at an input to processing logic 102. In one embodiment, the input may be configured to receive capacitance measurements indicating a plurality of row coordinates and a plurality of column coordinates. Alternatively, the input may be configured to receive row coordinates and column coordinates.

In some embodiments, processing logic 102 may be configured to generate (or to receive, e.g., from touch coordinate receiver 218) capacitance measurements that represent diff signals (also referred to herein as "diff signal values"). For example, processing logic 102 may be configured to determine a diff signal for a given sensor element as the difference between the settled/baseline (e.g., expected or fully charged) capacitance of a sensor element (e.g., when a conductive object is not in contact with the touch sensor and the touch sensor is not being scanned) and the capacitance of the sensor element that is measured as part of a scan operation (e.g., when a conductive object may or may not be in contact with the touch sensor). The capacitance used to compute a diff signal for a sensor element may be a self-capacitance and/or a mutual capacitance of the sensor element.

In various embodiments, the processing logic may compute the diff signals for each of the sensor elements in a touch sensor based on capacitance measurements that represent the self-capacitances and/or the mutual capacitances of the sensor elements. For example, a self-capacitance of a given sensor element may include a capacitance formed between the sensor element and a reference voltage (e.g., such as ground). A mutual capacitance of a given sensor element may include a capacitance formed between the transmit and receive electrodes that form the sensor element and/or one or more conductive objects (e.g., such as a stylus or user's finger) that are electrically insulated from the capacitive sensor element.

Single-Layer Touch Sensors

Attempts have been made in the past to reduce the number of layers, and thus the manufacturing costs, of touch sensors. In some embodiments, single layer touch sensors are suited only for single touch reception. These touch sensors typically use a series of electrodes the width of which linearly change from one end to the other end of an electrode. Using the signal variation along the electrode's length, the coordinate along the electrode's axis is determined. The coordinate in the perpendicular direction to the electrode's axis is determined by a conventional digitization method. In other embodiments, a single layer multiple-touch sensor uses an array of pads filling the sensor area, and each of the pads (or electrodes) are sensed individually in a self-capacitance sensing mode. Such embodiments usually require independent traces for each of the sensing pads and a very large number of measuring channels and pins on the controller chip to get an acceptable accuracy for even a small size sensor.

In some embodiments, a touch-sensor device includes a touch sensor that has a single layer active area. Additionally, the touch-sensor device is provided with a wiring scheme that minimizes the number of wires, as well as the traces, required to simultaneously detect multiple contacts (e.g., such as "touches"). As a result, the overall manufacturing costs of the touch sensor, and correspondingly of the touch sensor device, can be reduced.

FIGS. 3A and 3B are simplified views of a touch-sensor device 301 (e.g., such as a capacitance sensing device) according to an example embodiment. In this embodiment, touch-sensor device 301 is a "touchscreen" device that includes a touch sensor having an active area 302 and a non-active area 303. As used herein, "active area" and "touch-sensing area" of a touch sensor refer to an area of the sensor that can generate a signal, cause a capacitance change, or otherwise detect one or more contacts. "Non-active area" and "non-sensing area" of a touch sensor refer to an area that does not detect or otherwise respond to contacts. Touch-sensor device 301 includes a liquid crystal display (LCD) panel 304 arranged below a touch sensor 305 (e.g., such as a sensor array or assembly). As is commonly understood, the active area 302 may correspond to the size and shape of a transparent (e.g., visible) region of the touch sensor 305, while the non-active area 303 may correspond to a non-transparent (e.g., non-visible) region of the touch sensor 305 which may be covered by a casing (not shown) or other means that prevent the effect of contacts. Touch sensor 305 includes an overlay (or protective layer) 306 attached to a side thereof opposite the LCD panel by an adhesive 307. Touch-sensor device 301 also includes a flexible printed circuit (FPC) tail 308 extending therefrom, which may be used to route electrical signals to and from touch sensor 305.

Figure 3C:
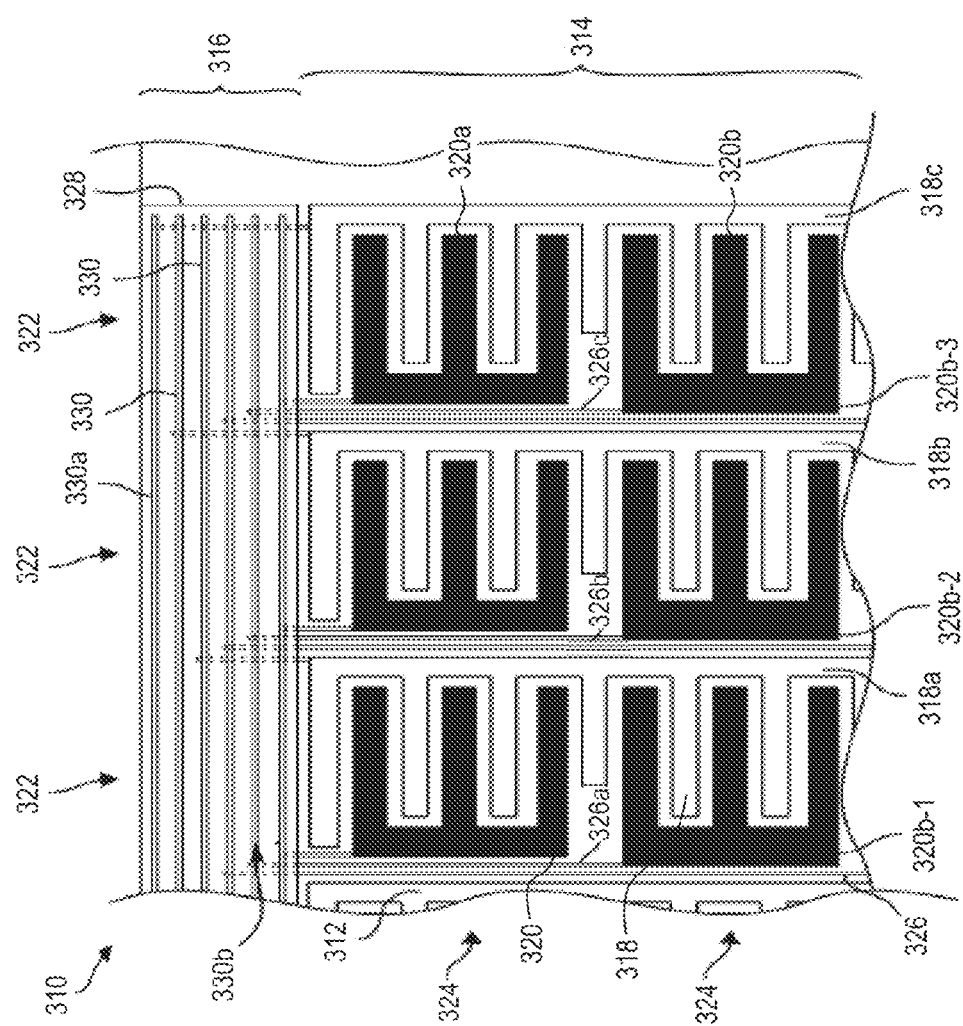
FIG. 3C illustrates a portion of a touch sensor according to an example embodiment.

FIG. 3C illustrates a portion of a touch sensor 310 (e.g., such as a capacitive sensor array) according to an example embodiment. Touch sensor 310 includes a substrate 312 having an active area (or central portion) 314 and a non-active area (or bezel portion) 316 near the edge(s) of substrate 312. Central portion 314 of substrate 312 may correspond to the active (e.g., touch-sensing) area of a touch-sensor device (e.g., such as area 302 of touch-sensor device 301 in FIG. 3A). Bezel portion 316 of substrate 312 may correspond to the non-active (e.g., non-sensing) area of the touch-sensor device (e.g., such as area 303 of touch-sensor device 301 in FIG. 3A). In some embodiments, substrate 312 is made of an electrically insulating material with high optical transmissivity, such as glass, polyethylene terephthalate (PET), or a combination thereof.

An array of electrodes is formed on central portion 314 of substrate 312, which includes a first set (or plurality) of electrodes 318 (also referred to as "first electrodes") and a second set (or plurality) of electrodes 320 (also referred to as "second electrodes"). First electrodes 318 and second electrodes 320 are all formed on the same (e.g., a single) layer of substrate 312, but without intersecting each other and while maintaining electrical (e.g., galvanic) isolation from each other. In some embodiments, in order to form the first and second electrodes, a layer of transparent conductive material, such as indium-tin oxide (ITO) or a silver nanoparticle film, may be deposited on (or over) substrate 312. As will be described in more detail hereinafter, first electrodes 318 may be used as transmit (TX) electrodes, and second electrodes 320 may be used as receive (RX) electrodes during scan operations that are performed on touch sensor 310. It should be understood, however, that these TX and RX roles are merely exemplary and may be reversed in various other embodiments.

First electrodes 318 are substantially "comb"-shaped having comb members facing leftward as shown in FIG. 3C. In the portion of touch sensor 310 depicted in FIG. 3C, three first electrodes 318 (e.g., 318a, 318b, and 318c) and two second electrodes 320 (e.g., 320a and 320b) are included. The three first electrodes are arranged substantially vertically and extend along substantially the entire length of central portion 314 of substrate 312. It should be understood, though, that other embodiments may use different numbers of first electrodes that may extend in directions other than vertical, and that in other embodiments one subset of the first electrodes may extend only about half-way down the length of the central portion with another subset of the first electrodes extending upward from a bezel portion at the bottom of the substrate.

According to the techniques for correcting tail effects described herein, a second electrode comprises one or more shaped portions, one or more primary traces, and at least one secondary trace, where the primary trace(s) and the shaped portion(s) are routed in the active (touch-sensing) area of the touch sensor. As used herein, a primary trace is also referred to as a "line" or a "trace line". A "shaped" portion of an electrode has width that is greater than the width of a primary trace and a geometric shape that is different from a substantially straight line. A shaped portion is electrically connected to a respective primary trace and each primary trace is electrically coupled to the secondary trace in a non-active (non-sensing) area of the touch sensor. A primary trace of a given second electrode is routed in the active area of the touch sensor along at least a portion of one or more other primary traces of one or more other second electrodes that are formed further away from a non-active area (e.g., a bezel portion of the touch sensor) than the given second electrode. Further, a primary trace of a given second electrode is routed in the active area along at least a portion of a given first electrode. A secondary trace, which electrically couples the primary trace(s) of a given second electrode, is routed in the non-active area (e.g., such as a bezel portion) of the touch sensor. Thus, a primary trace of a given second electrode can be affected by a contact from a conductive object (which can contribute to changes in the signals measured from the given second electrode during a scan operation) because the primary trace is routed in the active, touch-sensing area of the touch sensor. On the other hand, a secondary trace is typically not affected by such contact because the secondary trace is routed in the non-active, non-sensing area of the touch sensor and therefore does not have an effect on the signals measured from the second electrode during the scan operation.

As an illustration, in FIG. 3C first electrodes 318 are arranged in columns 322 and second electrodes 320 are arranged in rows 324, where each of the columns 322 includes one of the first electrodes 318 and each of the rows 324 includes one of the second electrodes 320. Each of second electrodes 320 includes substantially "E"-shaped portions that extend rightward as shown in FIG. 3C. Each of the "E"-shaped portions of a given second electrode 320 is interleaved with a respective one of the first electrodes 318 (e.g., in an interdigitated pattern). Within each row 324, the "E"-shaped portions of a given second electrode 320 are electrically coupled to each other, and each "E"-shaped portion is interleaved (e.g., inter-digitated) with the "comb"-shaped members of a respective first electrode 318. For example, second electrode 320b includes three "E"-shaped portions (e.g., 320b-1, 320b-2, 320b-3) each of which is electrically connected to a respective primary trace (e.g., 326a, 326b, 326c, correspondingly), where all the respective primary traces are electrically coupled to each other over a secondary trace (e.g., 330b) in the bezel portion 316. It is noted that the specific electrode patterns shown in FIG. 3C are merely exemplary and thus other electrode shapes and interleave patterns, which may not be inter-digitated, are possible and within the scope of the techniques described herein.

In FIG. 3C, the primary traces 326 coupled to the shaped portions of the second electrodes 320 are routed substantially in parallel and adjacent to each other. The primary traces of second electrodes that are further away from bezel portion 316 are longer and are routed adjacent to more shaped portions of other second electrodes than primary traces of second electrodes that are closer to the bezel portion.

The first electrodes 318, the second electrodes 320, and the primary traces 326 may be made of indium tin oxide (ITO) and may be formed in a substantially planar manner on the same (e.g., a single) substrate layer. That is, although not specifically shown in FIG. 3C, the first electrodes 318, the second electrodes 320, and the primary traces 326 may have substantially the same thickness (e.g., 300 Angstroms (Å)) and may lay in substantially the same plane.

As illustrated in FIG. 3C, an insulating material (or body or layer) 328 is formed or otherwise attached to the bezel (outer) portion 316 of substrate 312. The insulating material 328 covers the end portions of the primary traces 326 that extend onto the bezel portion 316, but it should be noted that the insulating material 328 does not extend over the central portion 314 of substrate 312. The insulating material 328 may be made of, for example, an epoxy or resin material and have a thickness of, for example, between 5 and 25 micrometers (μm) that is deposited on substrate 312. In some embodiments, the insulating material 328 may be a flexible substrate, such as a flexible printed circuit (FPC), attached to substrate 312. The insulating material 328 electrically separates a given secondary trace 330 from at least some of the primary traces 326. For example, in FIG. 3C, the insulating material 328 insulates the secondary trace 330b from the primary traces 326 connected to second electrode 320a and from the primary traces of those second electrodes 320 that are different from electrode 320b.

The secondary traces (or plurality of conductors) 330 are formed on the insulating material 328 in the bezel portion 316 of substrate 312. In one embodiment, the secondary traces 330 are made of silver. Of interest in the embodiment of FIG. 3C is that a given secondary trace 330 is electrically connected to all of primary traces 326 that are associated with a given second electrode 320 in a given one (and only one) of rows 324. Further, in the embodiment of FIG. 3C, a separate secondary trace 330 is electrically coupled to a corresponding one of first electrodes 318. For example, secondary trace 330a is coupled to first electrode 318c. To reduce the routing area in the bezel portion 316, in some embodiments the trace width and spacing of the secondary traces 330 in the bezel area may be minimized. For example, a metal trace line width of 10-50 μm and a spacing of 10-50 μm may be used in the bezel area.

It should be understood that touch sensor 310 may include an additional set of traces not shown in FIG. 3C. For example, an additional set of ground traces may be formed in the active area of touch sensor 310 and may be routed substantially in parallel to the first electrodes 318. Such ground trace may be used to provide a ground in order to electrically isolate a given first electrode 318 from the immediately neighboring/adjacent primary traces 326 that are connected to second electrodes 320. As such, each of the ground traces may be electrically connected to at least one of the secondary traces 330 that is coupled to the system ground.

In operation, the secondary traces 330 are coupled to (e.g., are in operable communication with) an electronic system (e.g., such as the system illustrated in FIG. 2) in order to perform scan operations on touch sensor 310. In a scan operation, touch sensor 310 is operated by providing a signal to each one (referred to as "the driven" TX electrode) of the first electrodes 318 in turn, while grounding the remaining first electrodes 318. Signals are induced in those second electrodes 320 (RX electrodes) that have shaped portions interleaved with the driven TX electrode because of the capacitive coupling therebetween. The signals induced in the RX electrodes are measured and/or recorded by a processing logic in the electronic system. The measured/recorded signals may change (from pre-determined baseline value(s)) due to the presence of a conductive object (e.g., such a finger or stylus) that is in contact with a portion of touch sensor 310. A signal change (e.g., from a baseline value) measured on the RX electrodes is indicative of change in the capacitance (e.g., in the "mutual capacitance") between one or more of the RX electrodes and the driven TX electrode. After measuring the signals on the RX electrodes, the scan operation continues by providing a signal to the next TX electrode and measuring the corresponding RX electrodes in the same manner.

FIGS. 4A-E illustrate alternative shapes, patterns, and arrangements of the first electrodes 318 and the second electrodes 320, according to various embodiments of the techniques described herein. For example, the embodiment shown in FIG. 4A includes a first electrode 318 and second electrodes 320 that include interleaved "spiral" structures, as opposed to the "comb" and "E" shaped structures previously discussed with respect to the first and second electrodes, respectively. However, it should be understood that other shapes, patterns, and arrangements may be used, as shown by the various alternative embodiments illustrated in FIGS. 4B, 4C, 4D, and 4E.

In some embodiments, different materials may be used to form the sensor (e.g., first and second) electrodes, such as copper, aluminum, silver, or any suitable conductive material that may be appropriately patterned. Furthermore, an FPC may be used to form the sensor electrodes. In such embodiments, the various conductive layers in the FPC may be appropriately configured to form the array of first and second electrodes as described above, as well as to form the primary traces thereof. As such, it should be understood that the electrodes, the traces, and the insulating material (or body) may all be formed by a single, appropriately configured FPC. As will be appreciated by one skilled in the art, such embodiments may be particularly applicable to non-transparent devices, such as mouse pads, track pads, touch pads, etc. Additionally, in some embodiments, the substrate may be made of other materials, such as any suitable plastic, including vinyl and polyamide, which may not be transparent, depending on the particular device.

In some embodiments, a touch sensor may be formed by laying out the sensor electrodes using alternative conductive materials such as metal mesh. In such embodiments, the sensor electrodes are formed by disposing metal mesh electrodes on PET substrate. In alternative embodiments, the metal mesh sensor electrodes may be disposed on glass substrate. In other embodiments, the sensor electrodes may be formed with silver nano-wires on PET or silver nano-wire on glass substrate. In other embodiments, a touch sensor may be formed by bonding a glass (or other transparent insulating) lens onto another glass with the sensor electrode pattern disposed on. In yet other embodiments, the touch sensor may be formed by bonding glass (or other transparent insulating material) onto a sheet of PET containing the sensor pattern.

Thus, embodiments described herein provide a touch-sensor device with a single-layer structure in the active area (or portion) of the touch sensor in the device, while a multi-layer structure may be used in the bezel (or other non-sensing) portions of the touch sensor for routing the traces. Such multi-layer routing allows the repeated use of the traces so that the touch sensor uses the minimum number of traces and the minimum number of pins on the electronic system which drives the touch-sensor device, thereby reducing the associated manufacturing costs.

Tail Effect

The tail effect in a single-layer touch sensor may be a parasitic signal increase or a parasitic signal decrease in one or more sensor elements in response to a contact by a conductive object (e.g., a stylus, a user's finger, etc.) with the touch sensor. In some embodiments, the tail effect for a given sensor element is caused by a parasitic signal coupling between a TX electrode and the primary trace of an RX electrode whose shaped portion is outside the actual contact area and is thus not affected by the contact.

The techniques for correcting tail effect described herein provide for analyzing the signal profile from a specific section of a touch sensor. The analysis uses linear approximation (e.g., based on the measured/derived signal values of sensor elements that are below some tail-effect threshold value) to compute adjustment values that correct the parasitic signal change of the tail effect, and subtracts the adjustment values from the measured/derived signal values before performing position calculation to compute the location coordinates of the contact.

Figure 5:
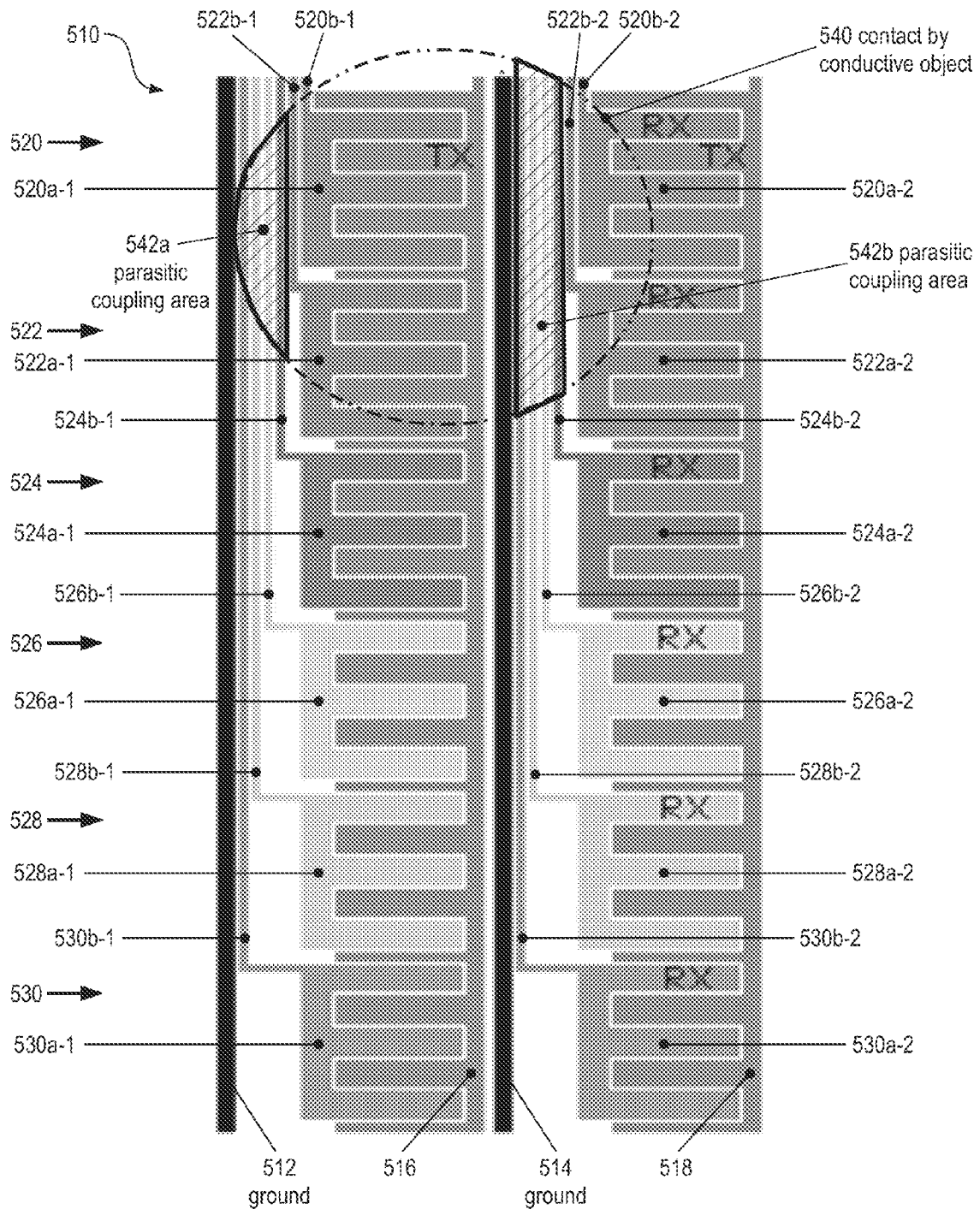
FIG. 5 illustrates parasitic signal coupling in a portion of a touch sensor panel with a single-layer, SLIM electrode pattern according to an example embodiment.

FIG. 5 illustrates parasitic signal coupling in a portion of a touch sensor panel with a single-layer electrode pattern in the touch-sensing area of the touch sensor. According to an example embodiment, portion 510 of a touch sensor includes ground traces 512 and 514, TX electrodes 516 and 518 (arranged as vertical columns), and RX electrodes 520, 522, 524, 526, 528, and 530 (arranged as horizontal rows). Ground traces 512 and 514 are disposed in the touch-sensing area of touch sensor portion 510 and are routed substantially in parallel with, and immediately adjacent to, the TX electrodes. A ground trace (e.g., such as ground trace 514) is used to provide a ground in order to electrically isolate a given TX electrode (e.g., such as TX electrode 516) from the neighboring/adjacent portions of RX electrodes (e.g., such as RX electrode portions 530a-2 and 530b-2, 528a-2 and 528b-2, 526a-2 and 526b-2, etc.) Each of TX electrodes 516 and 518 is disposed substantially vertically and includes substantially "comb"-shaped members that are interleaved with the shaped portions of RX electrodes 520-530. Each of RX electrodes 520, 522, 524, 526, 528, and 530 is disposed in its own row and, as illustrated, includes at least two substantially "E"-shaped portions each of which is electrically connected to its own corresponding primary trace, each of which in turn is electrically connected to the other primary traces of that RX electrode by a secondary trace (not shown) in the non-sensing (e.g., bezel) area of the touch sensor.

Specifically, RX electrode 520 includes shaped portion 520a-1 that is electrically connected to primary trace 520b-1 and shaped portion 520a-2 that is electrically connected to primary trace 520b-2. Similarly, RX electrode 522 includes shaped portion 522a-1 that is electrically connected to primary trace 522b-1 and shaped portion 522a-2 that is electrically connected to primary trace 522b-2. RX electrode 524 includes shaped portion 524a-1 that is electrically connected to primary trace 524b-1 and shaped portion 524a-2 that is electrically connected to primary trace 524b-2. RX electrode 526 includes shaped portion 526a-1 that is electrically connected to primary trace 526b-1 and shaped portion 526a-2 that is electrically connected to primary trace 526b-2. RX electrode 528 includes shaped portion 528a-1 that is electrically connected to primary trace 528b-1 and shaped portion 528a-2 that is electrically connected to primary trace 528b-2. Finally, RX electrode 530 includes shaped portion 530a-1 that is electrically connected to primary trace 530b-1 and shaped portion 530a-2 that is electrically connected to primary trace 530b-2.

FIG. 5 illustrates an operational scenario where a contact 540 by a conductive object is effected on touch sensor portion 510. As illustrated, contact 540 is located mostly over shaped portion 520a-1 of RX electrode 520 and a bit less so over shaped portion 522a-1 of RX electrode 522; in addition, contact 540 is located partially over shaped portion 520a-2 of RX electrode 520 and less so over shaped portion 522a-2 of RX electrode 522. Contact 540 is also located over, and affects, TX electrodes 516 and 518. As illustrated, however, contact 540 also capacitively affects the primary traces 524b-1, 526b-1, 528b-1, and 530b-1 (of RX electrodes 524, 526, 528, and 530, respectively) in parasitic coupling area 542a. Similarly, contact 540 capacitively affects the primary traces 524b-2, 526b-2, 528b-2, and 530b-2 (of RX electrodes 524, 526, 528, and 530, respectively) in parasitic coupling area 542b. Because of the parasitic coupling of contact 540 in areas 542a and 542b, the signal values read during a scan operation from RX electrodes 524, 526, 528, and 530 will register signal changes (from their respective baselines) even though the contact is not located over the shaped portions of RX electrodes 524, 526, 528, and 530 and thus the shaped portions of these RX electrodes are not affected by the contact. These signal changes represent the tail effect caused by the parasitic coupling in areas 542a and 542b. Hence, if the signal values read from RX electrodes 524, 526, 528, and 530 are not corrected for the signal changes caused by the tail effect in parasitic coupling in areas 542a and 542b, the position location of contact 540 on the touch sensor may be computed incorrectly (e.g., as being shifted away from its actual location).

As illustrated in FIG. 5, there is extra parasitic coupling on the primary traces of the RX electrodes whose shaped portions are not actually covered by the contact. However, these (not-affected-by-the-contact) shaped portions are interleaved with the shaped members of the corresponding TX electrodes to form the sensor elements from which distinct signal values are obtained. Thus, the tail effect causes more sensor elements to falsely register the contact because the primary traces connected to these sensor elements are directly affected by the contact (even though the sensor elements themselves are not in the area of the contact). Further, since the same primary traces are routed adjacent/next to each TX electrode, the more TX electrodes are covered by the contact the higher the tail effect will be.

As also illustrated in FIG. 5, the tail effect is "seen" (or registered) by downstream RX electrodes (and their sensor elements) when the routing of the RX electrodes goes from the top of the touch sensor to the bottom. The opposite will be true if the RX electrodes are routed from the bottom of the touch sensor to the top. In some embodiments, in order to minimize the total width of the area occupied by the primary traces of the RX electrodes (e.g., such as the width of parasitic coupling areas 542a and 542b), a touch sensor (e.g., such as a SLIM touch panel) may be double-routed—e.g., from a top bezel/non-sensing area and from a bottom bezel/non-sensing area of the touch sensor. This means that (about) half of the RX electrodes will have primary traces routed (e.g., extending down) from a top bezel, with the remaining RX electrodes having their primary traces routed (e.g., extending up) from a bottom bezel of the touch sensor.

Figure 6:
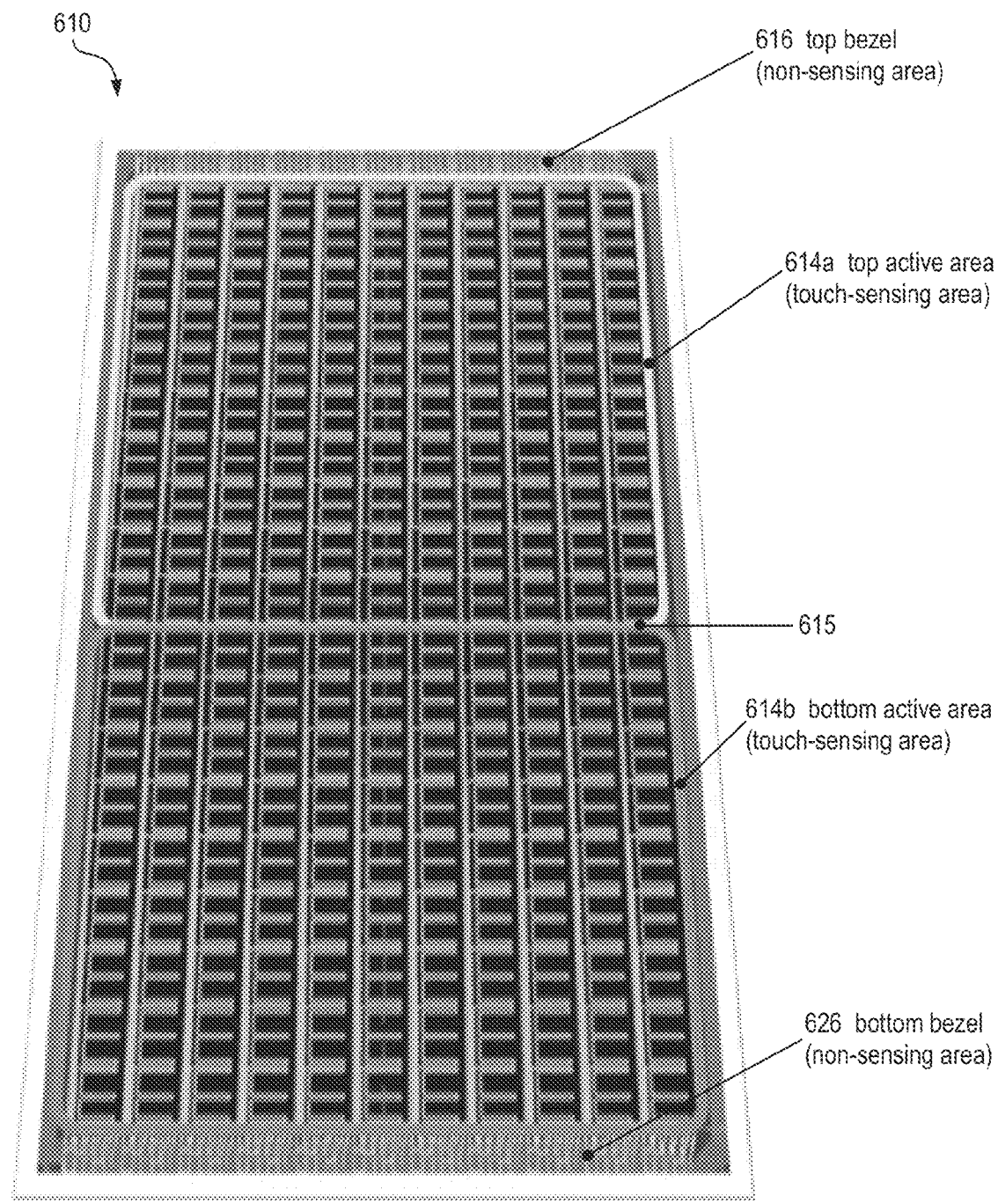
FIG. 6 illustrates a double-routed touch sensor panel with a SLIM electrode pattern according to an example embodiment.

An example of a double-routed, single-layer touch sensor panel is illustrated in FIG. 6. In the example embodiment of FIG. 6, touch sensor 610 includes top bezel (non-sensing) area 616, top active (touch-sensing) area 614a, bottom active (touch-sensing) area 614b, and bottom bezel (non-sensing) area 626. The RX electrodes in the top active area 614a are routed from the top bezel area 616, while the RX electrodes in the bottom active area 614b are routed from the bottom bezel area 626. In the embodiment illustrated in FIG. 6, the TX electrodes in the top active area 614a and the bottom active area 614b are both routed from the top bezel area 616. In other embodiments, similarly to the RX electrodes, the TX electrodes may also be spilt and double-routed from opposite non-sensing areas—e.g., if there is a need to reduce the RC constant of the sensor elements.

In the case of a double-routed touch sensor panel such as the panel in FIG. 6, a contact by a conductive object will cause a separate tail effect on each side of the panel. For example, a contact placed in the top active area 614a of touch sensor 610 will create a tail effect in sensor elements down from the contact area and towards the middle line 615 where the routing changes to bottom bezel routing. Similarly, a contact placed in the bottom active area 614b of touch sensor 610 will create a tail effect in sensor elements up from the contact area and toward the middle line 615.

Figure 7A:
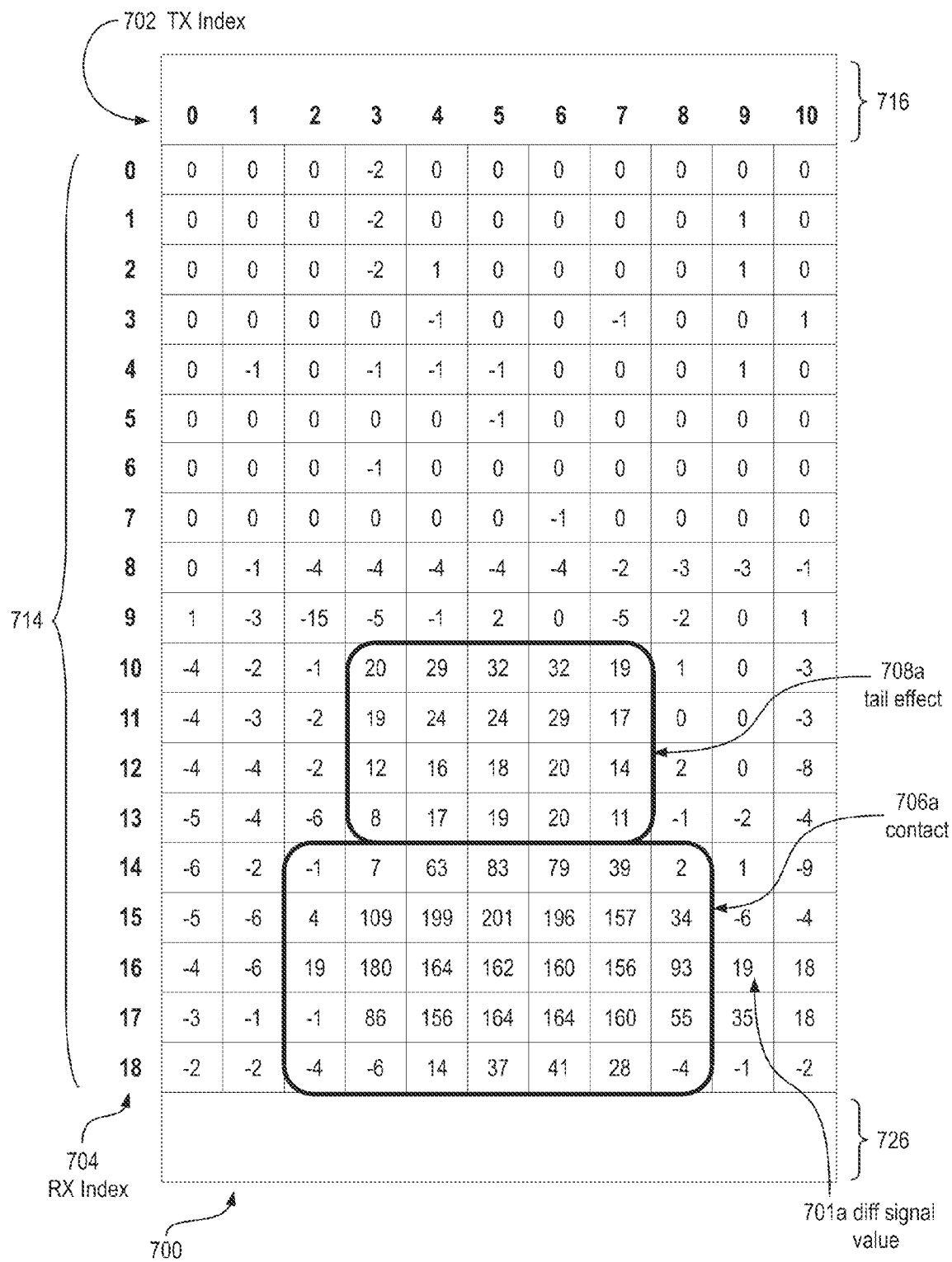

An example of a separate tail effect on each side of a double-routed, single-layer touch sensor panel is illustrated in FIGS. 7A and 7B. Specifically, FIGS. 7A and 7B illustrate an example data structure that stores signal values reflecting tail effects caused by conductive objects on each side of a double-routed touch sensor panel according to an example embodiment.

FIGS. 7A and 7B illustrate data structure 700 that stores diff signal values, where the signal values were derived from a plurality of measurements that were measured from the sensor elements of a sensor array during a certain scan operation (illustrated in FIG. 7A) and a different scan operation (illustrated in FIG. 7B). The sensor array includes active touch-sensing area (logically indicated by reference numeral 714), top non-sensing area (logically indicated by reference numeral 716), and bottom non-sensing area (logically indicated by reference numeral 726).

In FIGS. 7A and 7B, the sensor elements of the sensor array are represented logically as boxes formed by 11 TX electrodes and 19 RX electrodes. A sensor or processing logic (not shown) that operates the sensor array stores/associates a separate index value for each separate TX electrode, where the index values are arranged in a sequence representing a physical arrangement of the TX electrodes in the sensor array; similarly, the sensor or processing logic also stores/associates a separate index value for each separate RX electrode, where the index values are arranged in a sequence representing a physical arrangement of the RX electrodes in the sensor array.

For example, in FIGS. 7A and 7B TX index 702 is a sequence of integer values ranging from 0 to 10 that represent the 11 TX electrodes; similarly, RX index 704 is a sequence of integer values ranging from 0 to 18 that represent the 19 RX electrodes. In the embodiment illustrated in FIGS. 7A and 7B, RX electrodes with index values "0" to "9" are routed from the top non-sensing area (716) thereby forming the top portion of the sensor array, while the remaining RX electrodes with index values "10" to "18" are routed from the bottom non-sensing area (726) thereby forming the bottom portion of the sensor array.

FIGS. 7A and 7B also illustrates the diff signals, obtained by a corresponding scan operation, for each of the sensor elements represented in data structure 700. For example, in the scan operation of FIG. 7A, a diff signal 701a (having a value of "19") is measured or otherwise obtained for the sensor element formed by TX electrode with TX index of "9" and the shaped portion of RX electrode with RX index of "16". In the scan operation of FIG. 7B, a diff signal 701b (having a value of "1") is measured or otherwise obtained for the same sensor element (i.e., that is formed by TX electrode with TX index of "9" and the shaped portion of RX electrode with RX index of "16"). It is noted that since various embodiments may use sensor arrays with various numbers of transmit and receive electrodes and various numbering schemes for the corresponding TX and RX indexes, the techniques for correcting tail effect described herein are not limited to any particular number of electrodes. Thus, the sensor array and its TX and RX indexes corresponding to data structure 700 depicted in FIGS. 7A and 7B are to be regarded in an illustrative rather than a restrictive sense.

In FIG. 7A, the diff values for the sensor elements represented in data structure 700 are obtained by a scan operation at a given point in time. The diff values indicate that a contact 706a is present on the touch-surface in the bottom portion of the sensor array. The diff values also indicate that tail effect 708a is also present in the bottom portion of the array only. It is noted that the diff values represent the state of the sensor elements of the sensor array at the time the scan operation is performed—thus, the contact 706a illustrated in FIG. 7A may be a stationary contact (e.g., such as a tap) or may be part of a more complex gesture (e.g., such as a scrolling gesture).

In FIG. 7B, the diff values for the sensor elements represented in data structure 700 are obtained by a scan operation that is different than the scan operation reflected in FIG. 7A (e.g., at a different point in time). Referring to FIG. 7B, the diff values indicate that a contact 706b is present on the touch-surface in the top portion of the sensor array. The diff values also indicate that tail effect 708b is also present in the top portion of the sensor array only. The contact 706b illustrated in FIG. 7B may be a stationary contact (e.g., such as a tap) or may be part of a more complex gesture (e.g., such as a scrolling gesture).

It is noted that various different sensor designs are prone to the parasitic tail effect described above, except that the degree to which the tail effect is exhibited may vary from design to design. Thus, in various embodiments, the techniques for correcting tail effect described herein may be implemented for sensor arrays that were constructed according to various different design technologies. Such designs and technologies include, but are not limited to, single-solid-diamond design, MH3, and metal mesh.

Examples of Processing Tail Effect Data

The tail effect in single-layer touch sensors is proportional to the RX index of the RX electrodes under a contact, with the presumption that the RX index values increase in the direction away from the side of the touch sensor from which the RX electrodes are routed. For example, the further away the shaped portion of an RX electrode is from the actual contact, the more tail effect signal from parasitic coupling it gets. Referring to FIG. 5 as an example, even though shaped portions 530a-1 and 530a-2 are farther away from the contact 540, RX electrode 530 gets the most signal from parasitic coupling when compared to the other depicted RX electrodes at least because: (1) the primary trace portions 530b-1 and 530b-2 run a longer length along TX electrodes 516 and 518, respectively; and (2) when the conductive object 540 is present, it reduces the signal from all four shaped portions of RX electrodes that are directly affected (520a-1, 520a-2, 522a-1, 522a-2) proportionally with respect to the baselines of the corresponding sensor elements, and thus the bottom RX electrode 530 still gets the most signal from the parasitic coupling. To put it differently, RX electrode 520 gets the smallest signal increase because of parasitic coupling under contact 540 because this RX electrode has the shortest primary traces.

According to the techniques for correcting tail effect described herein, a given scan operation (also referred to as a scan "frame" or "cycle") obtains measurements for all sensor elements in the sensor array (e.g., by powering the TX electrodes and reading the signal on the RX electrodes). In some embodiments, obtaining the measurements may involve multiplexing several or all of the RX electrodes at the same time; when obtained, the set of measurements from all RX electrodes represents the measurements of a single scan operation. A processing logic determines the diff signal values from the measurements obtained by the scan operation—for example, by comparing the obtained measurements to the baseline values that are stored for the corresponding sensor elements. Then, assuming all sensor elements with signal strength below some threshold are caused by a tail effect, the techniques described herein provide for building/determining the parameters of an approximation line based on the determined diff signal values, using the determined parameters to compute for each affected sensor element an adjustment value that corresponds to the tail effect, and subtracting each computed adjustment value from the signal value of the corresponding sensor element thereby correcting for the tail effect.

It is noted that in double-routed touch sensor designs (which provide a touch sensor with two separately-routed portions), a separate approximation line with its own separate parameters may be used when correcting for tail effect in each of the two separately-routed portions. Such separate parameters would indicate approximation lines with different angles starting on the edge of each portion of the touch sensor and ending in the middle of the touch sensor. An example of such double approximation lines is illustrated in FIG. 8.

Figure 8:
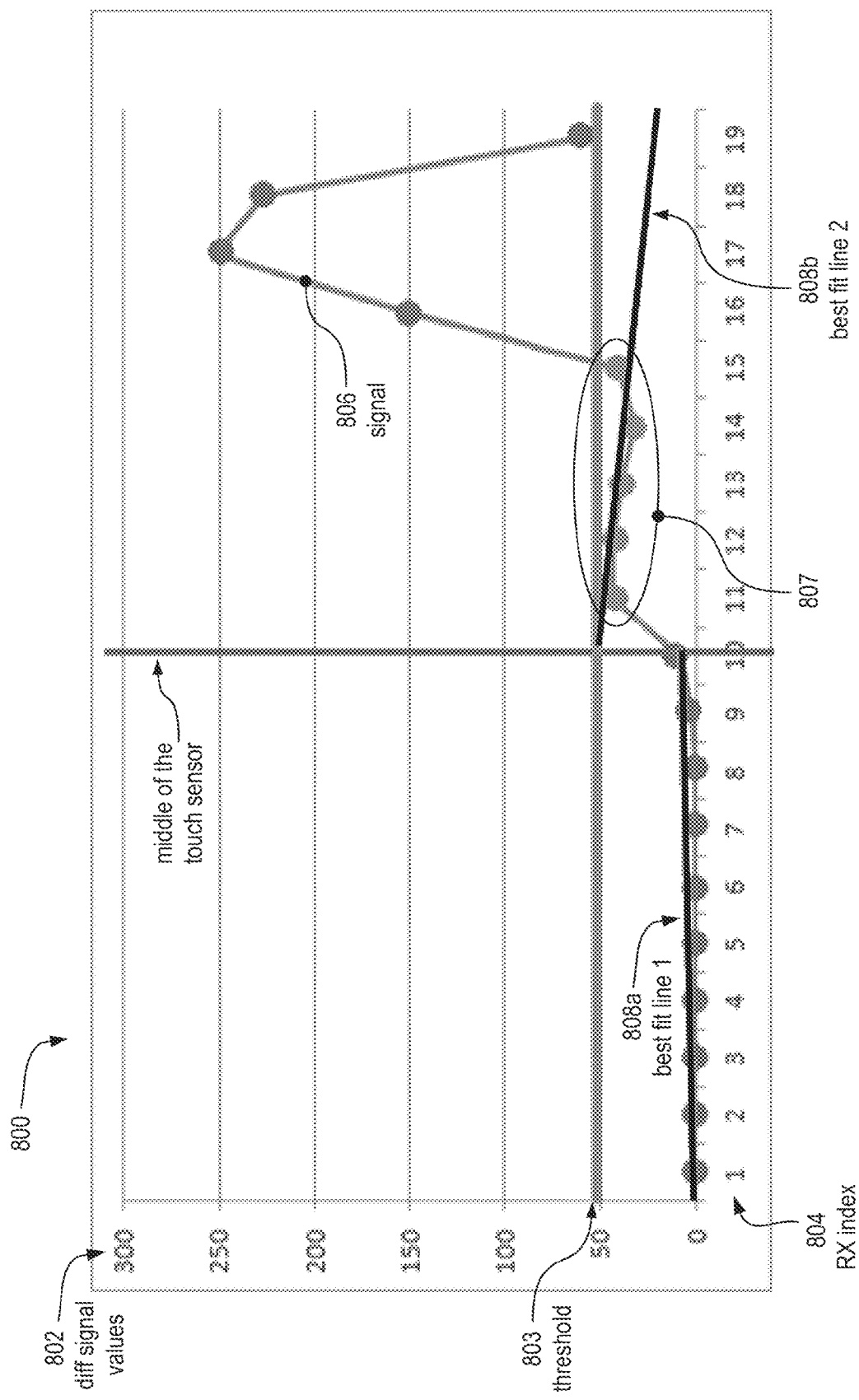
FIG. 8 is a graph illustrating an example of a tail effect correction on a double-routed touch sensor panel according to an example embodiment.

FIG. 8 is a graph illustrating an example of a tail effect correction for a certain middle TX electrode on a double-routed touch sensor panel. In graph 800, signal 806 is detected by a certain scan operation from the double-routed touch sensor and is plotted along an X-axis representing RX index values 804 and a Y-axis representing diff signal values 802. A tail-effect threshold 803 defines the diff signal level (around "55" or so) that is likely to be a tail effect. The techniques described herein are used to determine the parameters (e.g., angle or slope) of best-fit line 808a for the top portion of the touch sensor and best-fit line 808b for the bottom portion of the touch sensor. As illustrated in FIG. 8, line 808a has a different slope than line 808b, and both of these lines extend from their respective edges of the touch sensor towards its middle (around RX electrode with RX index value of "10"). Reference numeral 807 indicates the diff signals from the set of RX electrodes that are affected by the tail effect in the bottom portion of the touch sensor.

In some embodiments, the tail-effect threshold may depend either on a contact threshold setting for the touch sensor or on absolute peak signal as a certain percentage of it. In some embodiments, it makes more sense to make the tail-effect threshold value dependent on absolute peak signal as the tail effect is proportional to the absolute peak signal value. For example, in one particular embodiment, the tail-effect threshold is set as a percentage of the contact determination threshold of the touch sensor. In this particular embodiment, the determination contact threshold is adaptive and depends on the maximum peak value detected by the underlying scan operation, and a typical setting for the tail-effect threshold is two-thirds (⅔) of the adaptive contact threshold value.

More generally, if a touch sensor is intended to be operated with small objects (e.g., such as small fingers or styli), then a dynamic/adaptive type of threshold is preferably used since the differences between the scan operation measurements (e.g., raw counts) from an actual touch and from a tail effect are not that big. For example, a contact from a 4 mm finger may generate a signal that is about the same in magnitude as the signal from the tail effect of a larger finger (e.g., a 20 mm finger). Thus, the use of a dynamic/adaptive contact determination threshold is useful—initially a very low detection threshold may be set to detect the contact by the small finger, and thereafter the contact determination threshold may be dynamically adjusted specifically for this contact based on the maximum peak signal value (e.g., raw counts) that is actually measured for the contact. In this example, the tail-effect threshold may be set as 50% less than the maximum peak signal actually detected. In this manner, the tail-effect threshold is "adapted" for each contact that is detected.

In some embodiments, if a touch sensor is intended to be operated with bigger objects (e.g., such as normal or fat fingers), then a fixed tail-effect threshold is preferably used since the differences between the magnitude of an actual touch and the magnitude of the tail effect signal (due to parasitic coupling) are significant. For example, threshold 803 in FIG. 8 represents a fixed threshold value of about "55" that may be used to determine tail-effect signals—e.g., diff signal values that are above "0" and below "55" may be considered as tail effect signals.

According to the techniques for correcting tail effect described herein, the diff signals of the sensor elements that are below a (fixed or adaptive) tail-effect threshold are used in the linear approximation computation for the given TX electrode along which these sensor elements are formed.

In some embodiments, equation 1 below is used to determine a linear approximation (e.g., such as a best fit line) of the dependence between diff signals due to the tail effect and the index values of RX electrodes that form the sensor elements corresponding to the diff signals:

$$S_i = a * rxIndex + b \quad (1)$$

where:

b is an intercept (or offset) parameter equal (or approximately equal) to "0" since the tail effect signal does not exist (or is negligible) at the edge of the touch sensor from which the RX electrodes are routed (e.g., because RX electrodes at that edge do not have a significant length of primary traces exposed to the contact), rxIndex is the RX index value of one (e.g., the $i^{th}$) RX electrode that forms one (e.g., the $i^{th}$) individual sensor element along a given TX electrode, a is a constant slope (or angle) parameter value that defines the skew (slope) of the approximation best fit line for the given TX electrode (it is noted that the slope parameter value is unique for each TX electrode and for each portion of the touch sensor from which RX electrodes are routed if a double-routed touch sensor design is used), and $S_i$ represents the adjustment value for one (e.g., the $i^{th}$) individual sensor element, where this adjustment value corresponds to the tail effect signal at the $i^{th}$ sensor element (as determined based on the approximation best fit line) and should be subtracted from the diff signal of that sensor element in order to correct for the tail effect.

In some embodiments, the value of slope parameter (or coefficient) a may be determined by using equation 2 below:

$$a = \frac{\sum_{i=0}^{N} s_i}{\sum i}, \{s_i > 0, s_i < \text{threshold}\} \quad (2)$$

where $s_i$ is the diff signal value obtained from one (e.g., the $i^{th}$) individual sensor element formed by one (e.g., the $i^{th}$) RX electrode along the given TX electrode, i is the RX index value of one (e.g., the $i^{th}$) individual sensor element (along the given TX electrode) whose diff signal value $s_i$ is greater than "0" and less than the tail-effect threshold that is being used, N is the number of sensor elements along the given TX electrode that have diff signal values greater than "0" and less than the tail-effect threshold, $\Sigma_{i=0}^{N} s_i$ is the sum of the diff signal values for the sensor elements along the given TX electrode that have diff signal values greater than "0" and less than the tail-effect threshold, and $\Sigma i$ is the sum of the RX index values of the sensor elements along the given TX electrode that have diff signal values greater than "0" and less than the tail-effect threshold. Thus, according to equation 2, only sensor elements with diff signals having values between "0" and "threshold" are used to determine the parameters of the approximation best fit line, with the rest of the sensor elements and their RX index value being skipped from the calculation.

An example of an approximation best-fit line for a double-routed touch sensor is illustrated in FIG. 8 (e.g., such as best fit line 808b). As illustrated in FIG. 8, only the sensor elements corresponding to the diff signal values indicated by reference numeral 807 are used in determining the parameters of the best fit line 808b.

In some embodiments, after the slope parameter (or coefficient) a is determined (e.g., according to equation 2 above) for a given TX electrode, the adjustment value $S_i$ is computed for the corresponding (e.g., $i^{th}$) sensor element (e.g., according to equation 1 above). The tail effect is then corrected by subtracting the adjustment value $S_i$ from the diff signal value $s_i$ obtained for the corresponding (e.g., $i^{th}$) sensor element by using equation (3) below:

$$\text{Diff}_{rxIndex} = S_{rxIndex} - a*rxIndex \quad (3)$$

(which is equivalent to $S_{i-corrected} = S_i - S_i$)
where
a*rxIndex (e.g., $S_i$) is the adjustment value that corresponds to the tail effect for the sensor element formed along the given TX electrode by the RX electrode with RX index value of "rxIndex" (e.g., the $i^{th}$ sensor element), $S_{rxIndex}$ (e.g., $s_i$) is the originally obtained diff signal value for the for the sensor element formed along the given TX electrode by the RX electrode with RX index value of "rxIndex" (e.g., the $i^{th}$ sensor element), and $\text{Diff}_{rxIndex}$ (e.g., $S_{i-corrected}$) is the tail-effect corrected diff signal value for the sensor element formed along the given TX electrode by the RX electrode with RX index value of "rxIndex" (e.g., the $i^{th}$ sensor element).

In the example illustrated in FIG. 8, the left side (e.g., the top portion) of the touch sensor has received almost no signal from a contact, so the tail effect correction for this side is minimal. On the right side (e.g., the bottom portion) of the touch sensor, a tail effect from a contact was observed and the signal from it needs to be subtracted based on the parameters of best fit line 808b according to the techniques described herein. The resulting signal (as corrected for the tail effect) is plotted on the FIG. 9.

Figure 9:
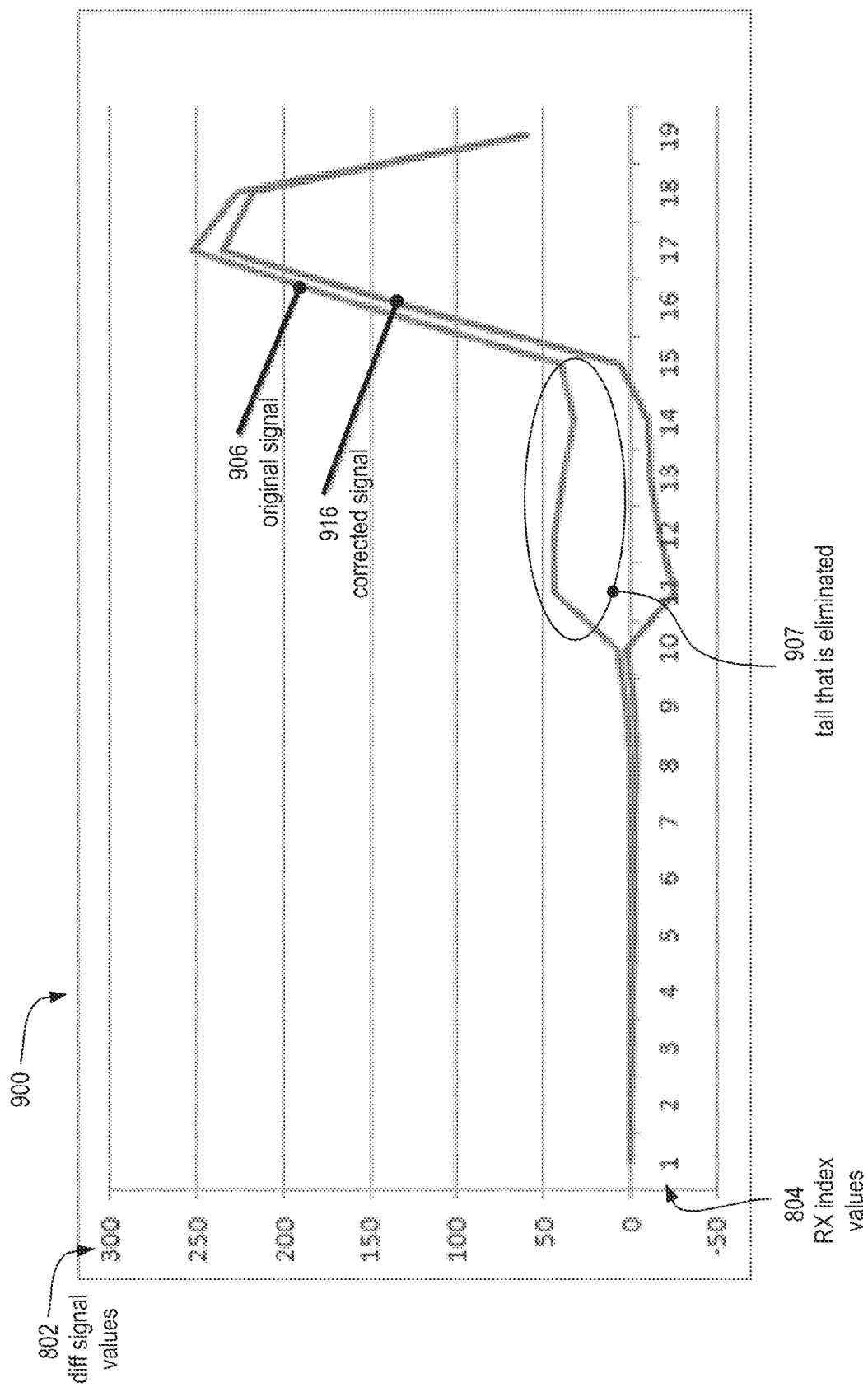
FIG. 9 is a graph illustrating a comparison of the tail-effect signal and a corrected signal for the double-routed touch sensor panel illustrated according to the example embodiment of FIG. 8.

FIG. 9 is a graph illustrating a comparison of a tail-effect signal and a corrected signal on a double-routed touch sensor panel of FIG. 8. In graph 900, the original signal 906 (e.g., as detected by a certain scan operation from the double-routed touch sensor) and the corrected signal 916 are plotted along an X-axis representing RX index values 804 and a Y-axis representing diff signal values 802. As illustrated in FIG. 9, the tail effect signal 907 is eliminated from the original signal 906, and no more tail is exposed in the corrected signal 916. Occasionally, in some embodiments the tail effect correction may produce negative signal values for the sensor elements where the tail effect was detected; however, this does not matter for the position (e.g., location coordinates) calculation since the position calculation algorithm in these embodiments zeros out all negative diff signal values.

In some embodiments, the tail effect correction is applied only for performing position calculation for a detected contact, and the tail effect correction should be reverted after the position calculation is completed. This is needed in order to maintain the correct baseline values for the sensor elements in the touch sensor in reference to the actual measured signal from a given scan operation, and make sure that the input data for the scan operation will have the same visible tail effect.

In some embodiments, reverting the tail effect correction may be performed by using equation 4 below:

$$\text{Diff}_{rxIndex} = S_{rxIndex} + a*rxIndex \quad (4)$$

(which is equivalent to $S_i = S_{i-corrected} + S_i$)
where
a*rxIndex (e.g., $S_i$) is the adjustment value that corresponds to the tail effect for the sensor element formed along the given TX electrode by the RX electrode with RX index value of "rxIndex" (e.g., the $i^{th}$ sensor element), $S_{rxIndex}$ (e.g., $s_{i-corrected}$) is the currently-stored, tail-effect corrected diff signal value for the for the sensor element formed along the given TX electrode by the RX electrode with RX index value of "rxIndex" (e.g., the $i^{th}$ sensor element), and $\text{Diff}_{rxIndex}$ (e.g., $S_i$) is the reverted (e.g., original) diff signal value for the sensor element formed along the given TX electrode by the RX electrode with RX index value of "rxIndex" (e.g., the $i^{th}$ sensor element).

This reversion of the tail-effect correction is applied individually for each TX electrode and for each portion of the touch sensor from which RX electrodes are routed (e.g., if a double-routed touch sensor design is used).

An example of a tail-effect corrected data, which was obtained experimentally from a certain embodiment, is illustrated in FIGS. 10A and 10B. Specifically, FIG. 10A illustrates data structure 1000 that stores diff signal values that reflect a tail effect caused by a conductive object on a double-routed touch sensor. FIG. 10B illustrates the same data structure 1000 that stores signal values that are adjusted with a correction for the tail effect. In FIGS. 10A and 10B, the sensor elements of the touch sensor are represented logically as boxes formed by 11 TX electrodes and 19 RX electrodes, where TX index 1002 is a sequence of integer values ranging from 0 to 10 that represent the 11 TX electrodes, and RX index 1004 is a sequence of integer values ranging from 0 to 18 that represent the 19 RX electrodes. In the embodiment illustrated in FIGS. 10A and 10B, RX electrodes with index values "0" to "9" are routed from a top non-sensing area thereby forming the top portion of the touch sensor, while the remaining RX electrodes with index values "10" to "18" are routed from a bottom non-sensing area thereby forming the bottom portion of the touch sensor.

In FIG. 10A, the diff signal values for the sensor elements represented in data structure 1000 are obtained by a scan operation at a given point in time. The diff signal values indicate that a contact is present in contact area 1006a in the bottom portion of the touch sensor. The diff signal values also indicate that a tail effect is present tail effect area 1008. In FIG. 10B, the diff values for the sensor elements represented in data structure 1000 have been corrected for the tail effect 1008 according to the techniques described herein. For example, adjustment values corresponding for the tail effect have been computed for the sensor elements in the touch sensor, and these adjustment values have been subtracted from the corresponding diff signal values stored in data structure 1000. As a result, in FIG. 10B data structure 1000 stores the corrected diff signal values for the sensor elements in contact area 1006b and in the corrected tail area 1018. Thus, FIG. 10A shows the initial signal map with the tail effect being present, while FIG. 10B shows the corrected signal map with the tail effect being eliminated according to the techniques described herein. After the tail effect correction is applied, as illustrated in FIG. 10B the position of the object in contact with the touch sensor is right in the middle of contact area 1006b.

In embodiments that use double-routed touch sensors, the RX index value (e.g., such as the "rxIndex" value used in equations 1, 3, and 4 above) should be always "0" at the end of the touch sensor (even if this RX index value corresponds to the last RX electrode in the sequence), and the closest RX electrode (or sensor element) to the middle of the touch sensor should have an RX index value equal to this RX electrode's incremental number from the edge of the touch sensor. In other words, for the purpose of the tail-effect correction computations, the indexing of the RX electrodes should start from "0" and be incremented from that side of the touch sensor from which the RX electrodes are routed. Thus, in the case of a double-routed touch panel, a re-mapping of the RX index values of RX electrodes may be needed for the purposes of the tail-effect correction computations described herein (e.g., as in equations 1, 3, and 4 above). For example, with respect to FIG. 10A, the RX index values "10" to "18" (for the bottom nine RX electrodes) should be re-mapped to values "9" to "0", respectively, prior to computing the tail effect corrections. This is but one way in which the techniques described herein can preserve the dependency that exists between tail effect and RX index values in single-layer touch sensors—namely, that the tail effect increases proportionally to the increase of the RX index values of the RX electrodes under a contact.

Examples of Methods for Correcting Tail Effect

Figure 11:
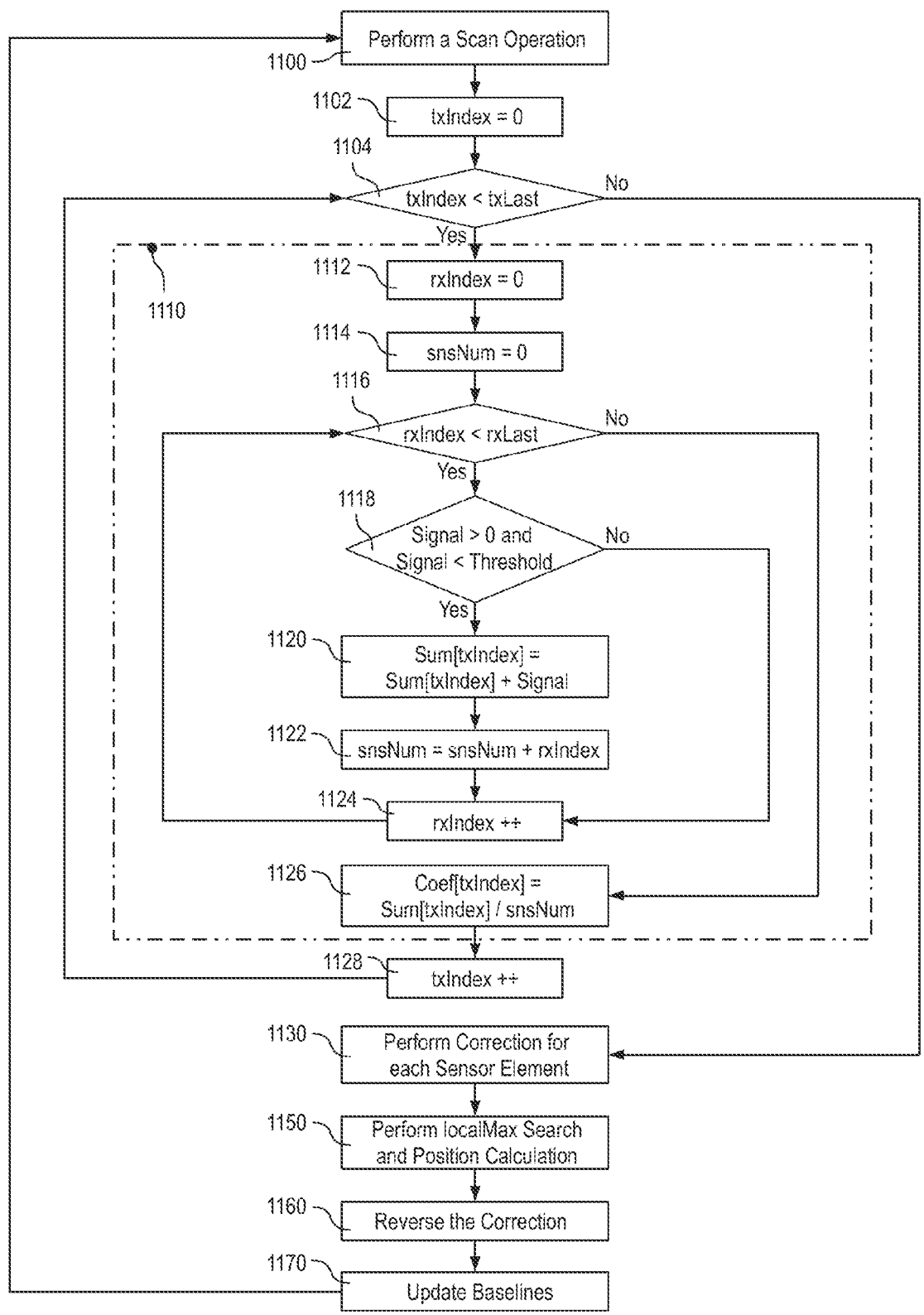
FIG. 11 illustrates a method for correcting tail effect according to an example embodiment.

FIG. 11 illustrates an example method for correcting tail effect. The steps of the method in FIG. 11 are described hereinafter as being performed by a processing logic (e.g., such as processing logic 102 in FIG. 1). It is noted, however, that various implementations and embodiments may use various, and possibly multiple, components to perform the operations of the method in FIG. 11. For example, in various embodiments a processing logic may be implemented in various ways including, but not limited to: as a set of stored software and/or firmware instructions which, when executed by one or more processors, are operable to perform one or more operations; as one or more software components (e.g., software modules, libraries of functions, compiled and/or interpretable object-oriented classes, dynamically linked libraries, and the like) that are executable by one or more computing devices; and as any combination(s) of one or more software components and one or more hardware components (e.g., processors, microcontrollers, Application-Specific Integrated Circuits (ASICs), and the like). In another example, in various embodiments a processing logic may be implemented in a single integrated component or its functionality may be spread across two or more components that may perform some additional operations and functionalities. Thus, the description hereinafter, of the method in FIG. 11 as being performed by a processing logic, is to be regarded in an illustrative rather than a restrictive sense.

In blocks 1100 to 1170, a processing logic performs a scan operation. In block 1100, as part of the scan operation the processing logic receives a plurality of measurements that are measured from a sensor array. The measurements are affected by a contact at the touch-surface of the sensor array by a conductive object (e.g., such as a stylus or user's finger). In some embodiments, the measurements received by the processing logic may include diff signal values for all (or a portion) of the sensor elements in the sensor array; in other embodiments, the processing logic may receive raw measurements (e.g., raw signal counts) from the sensor elements and may compute the corresponding diff signal values.

After receiving and/or computing the diff signal values corresponding to the received measurements, in block 1102 the processing logic performs an operation that initializes to zero a variable ("txIndex"), which denotes the TX index value of the current TX electrode for which computations are being performed.

In block 1104, the processing logic determines whether there are any remaining TX electrodes which need to be processed. For example, the processing logic performs a comparison operation to compare the value stored in the "txIndex" variable to a variable or constant ("txLast"), which denotes the total number of TX electrodes that need to be processed as part of the scan operation (e.g., such as the total number of TX electrodes in the sensor array). If the "txIndex" variable is less than the "txLast" variable, then at least the current TX electrode still needs to be processed, and the processing logic continues to perform the operations in blocks 1112 to 1128. If the "txIndex" variable is not less than the "txLast" variable, then the diff signal values for the sensor elements of all TX electrodes have been processed, and the processing logic continues to perform the operations in block 1130.

Block 1110 includes blocks 1112 to 1126, which include the operations that the processing logic performs to compute (e.g., according to equation 2 above) the slope parameter value a of the best fit line that approximates the tail effect signal for the current TX electrode (that is indicated by the "txIndex" variable). If the sensor array is double-routed, the processing logic performs the operations in block 1110 (e.g., the operations in blocks 1112 to 1126) twice—i.e., once for each portion of the sensor array from which RX electrodes are routed. It is noted that when performing these operations for the bottom portion of the sensor array, the RX index values of the RX electrodes routed from this portion may need to be re-mapped as described above (e.g., in order to preserve the dependency that exists between the tail effect and the RX index values).

In block 1112, the processing logic performs an operation that initializes to zero a variable ("rxIndex"), which denotes the RX index value of the current RX electrode (along the current TX electrode) for which computations are being performed.

In block 1114, the processing logic performs an operation that initializes to zero a variable ("snsSum"), which denotes the sum of the RX index values of the sensor elements (formed along the current TX electrode) that are included in computing the slope parameter (or coefficient) value a for the current TX electrode.

In block 1116, the processing logic determines whether there are any remaining RX electrodes that need to be processed for the current TX electrode. For example, the processing logic performs a comparison operation to compare the value stored in the "rxIndex" variable to a variable or constant ("rxLast"), which denotes the total number of RX electrodes that need to be processed for the current TX electrode. If the "rxIndex" variable is less than the "rxLast" variable, then at least the current RX electrode still needs to be processed and the processing logic continues to perform the operations in blocks 1118 to 1124. If the "rxIndex" variable is not less than the "rxLast" variable, then the diff signal values from all RX electrodes along the current TX electrode have been processed, and the processing logic continues to perform the operations in block 1126 (which compute the slope parameter value a for the current TX electrode).

In block 1118, the processing logic determines whether the diff signal value for the current RX electrode is to be included in the computation of the slope parameter value a for the current TX electrode. For example, if the diff signal value for the current RX electrode is greater than "0" and less than the tail-effect threshold, the processing logic includes this diff signal value in the computation. It is noted that this diff signal value is actually the diff signal value for the "current" sensor element that is formed by the current RX electrode (as indicated by the "rxIndex" variable) and the current TX electrode (as indicated by the "txIndex" variable). To make the determination, the processing logic may perform the following operation (which is a boolean operation with comparison-operation operands):

$$\text{Signal} > 0 \text{ and Signal} < \text{Threshold}$$

where "Signal" is a variable that stores the diff signal value of the current sensor element, and "Threshold" is a variable that stores the (fixed or adaptive) tail-effect threshold that is being used for the scan operation being processed. If the "Signal" variable is between "0" and the "Threshold" variable, then the current sensor element needs to be included in the computation of the slope parameter value a for the current TX electrode and the processing logic continues to perform the operations in blocks 1120 and 1122. If the "Signal" variable is not between "0" and the "Threshold" variable, then the current sensor element needs to be skipped/excluded from the computation and the processing logic continues to perform the operation in blocks 1124.

In block 1120, the processing logic determines the sum of the diff signal values of the sensor elements that are included in the computation of the slope parameter value a for the current TX electrode. For example, the processing logic adds the diff signal value of the current sensor element (which is formed by the current RX electrode indicated by the "rxIndex" variable and the current TX electrode indicated by the "txIndex" variable) to the current running sum of diff signal values that have been processed so far for the current TX electrode. To perform the addition, the processing logic may perform the following operation $$\text{Sum}[tx\text{Index}]=\text{Sum}[tx\text{Index}]+\text{Signal}$$

where "Sum [txIndex]" is a variable that stores the running sum of diff signal values for the current TX electrode (e.g., diff signal values for sensor elements formed by RX electrodes that have been processed so far for the current TX electrode), and "Signal" is a variable that stores the diff signal value of the current sensor element that is being processed.

In block 1122, the processing logic determines the sum of the RX index values of the sensor elements that are included in the computation for the current TX electrode (e.g., per equation 2 above.) For example, the processing logic adds the RX index value to the current running sum of the RX index values of the sensor elements, formed along the current TX electrode, that are included in computing the slope parameter value a for the current TX electrode. To perform the addition, the processing logic may perform the following operation $$sns\text{Num}=sns\text{Num}+rx\text{Index}$$

which adds the "rxIndex" variable to the "snsNum" variable, thereby effectively adding the RX index value of the current electrode to the running sum of the RX index values of the sensor elements that have been processed so far for the current TX electrode.

In block 1124, the processing logic sets the RX index value of the next RX electrode that needs to be processed and continues to perform the operation in block 1116. For example, the processing logic performs the operation $$rx\text{Index}++$$

which adds "1" to the "rxIndex" variable in order to indicate that the next RX electrode now becomes the current RX electrode for processing; thereafter, the processing logic continues with the operation in block 1116.

After the diff signal values from all RX electrodes along the current TX electrode have been processed, in block 1116 the processing logic determines that the current "rxIndex" variable is not less than the "rxLast" variable. Thus, the processing logic continues with the operations in block 1126.

In block 1126, the processing logic computes the slope parameter value a for the current TX electrode, and stores the value of this parameter in association with the current TX electrode. For example, the processing logic performs the operation $$\text{Coef}[tx\text{Index}]=\text{Sum}[tx\text{Index}]/sns\text{Num}$$

where "Coef[txIndex]" is a variable that stores the slope parameter value a for the current TX electrode, "Sum [txIndex]" is the variable that stores the sum of the diff signal values for the sensor elements along the current TX electrode that are used to correct the tail effect, and "snsNum" is the variable that stores the sum of the RX index values of the sensor elements that that are used to correct the tail effect for the current TX electrode.

In block 1128, the processing logic sets the TX index value of the next TX electrode that needs to be processed and continues to perform the operation in block 1104. For example, the processing logic performs the operation $$tx\text{Index}++$$

which adds "1" to the "txIndex" variable in order to indicate that the next TX electrode now becomes the current TX electrode for processing; thereafter, the processing logic continues with the operation in block 1104.

After the diff signal values for all TX electrodes have been processed, in block 1104 the processing logic determines that the current "txIndex" variable is not less than the "txLast" variable. Thus, the processing logic continues with the operations in block 1130.

In block 1130, the processing logic determines the adjustment values corresponding to the tail effect for the sensor elements on each TX electrode, and then corrects the diff signal values for these sensor elements on each TX electrode by subtracting from each such diff signal value its respective adjustment value. Two example methods for adjusting the diff signal values of sensor elements for tail effect are described below with respect to FIGS. 12 and 13.

In block 1150, the processing logic uses the tail-effect-corrected signal values to perform a localMax search and to calculate the location position of the conductive object on the sensor array. For example, in some embodiments the processing logic may search a data structure that stores the tail-effect-corrected signal values for single local maximums that are over a certain local-max threshold, where a single local maximum is a signal value that is larger than the signal values surrounding it in the data structure. The processing logic may compare each signal value to each of its neighbors, and may decide that a given signal value is a local maximum when none of its neighbors have a higher value. Thereafter, the processing logic uses (e.g., in a centroid location algorithm) the information about the found local maximums in order to calculate the contact position (e.g., such as touch coordinates and/or location centroid) of the conductive object on the sensor array.

In some embodiments, the tail effect correction may be needed only in the phase that calculates the location position of the conductive object on the sensor array. Thus, after position calculation is completed in these embodiments, the processing logic may perform the operations in block 1160 to reverse the tail-effect correction for each TX electrode. For example, in these embodiments the processing logic may perform the computations described for equation 4 above in order to restore, in the corresponding data structure, the original diff signal values that were received/obtained as part of the scan operation in block 1100. Such tail-effect reversion will ensure that any subsequent downstream processing based on the data stored in the data structure is performed correctly.

In some embodiments, in block 1170 the processing logic may (optionally) update the baseline values that are stored for the sensor elements of the sensor array. Typically, such baseline values are stored in firmware and are periodically maintained in order to ensure accurate operation of the sensor array. For example, since the conditions (e.g., temperature, humidity, etc.) in which a device operates may change, at least some scan operations may be configured to periodically compute and apply corrections to the stored baseline values.

After reversing the tail-effect correction and/or updating the baseline values, the processing logic proceeds back to block 1100 and continues with processing the next scan operation.

Figure 12:
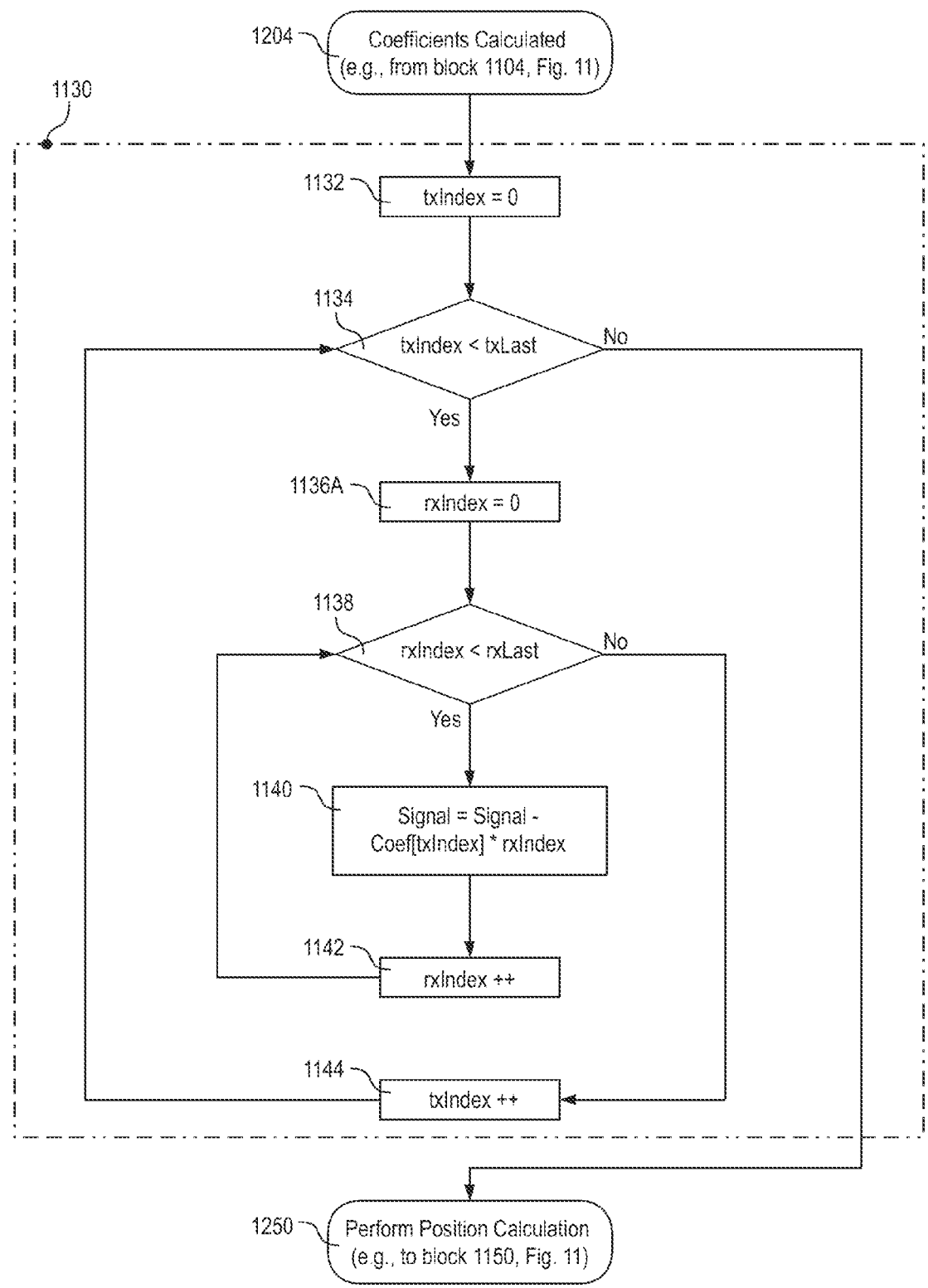
FIG. 12 illustrates an example method of adjusting signal values for tail effect according to some embodiments (e.g., such as the example embodiment illustrated in FIG. 11).

FIG. 12 illustrates an example method of adjusting signal values for tail effect according to some embodiments. For example, the method of FIG. 12 may be performed as part of the operations in block 1130 of FIG. 11 described above. The steps of the method in FIG. 12 are described hereinafter as being performed by a processing logic (e.g., such as processing logic 102 in FIG. 1). It is noted, however, that various implementations and embodiments may use various, and possibly multiple, components to perform the operations of the method in FIG. 12. For example, in various embodiments a processing logic may be implemented in various ways including, but not limited to: as a set of stored software and/or firmware instructions which, when executed by one or more processors, are operable to perform one or more operations; as one or more software components that are executable by one or more computing devices; as any combination(s) of one or more software components and one or more hardware components; and as a single integrated component or as two or more components that can perform additional operations. Thus, the description hereinafter, of the method in FIG. 12 as being performed by a processing logic, is to be regarded in an illustrative rather than a restrictive sense.

At block 1204, the slope parameter (or coefficient) values a for the TX electrodes of the sensor array have already been computed and stored in association with their corresponding TX electrodes. For example, as part of any given scan operation, the processing logic may maintain (in memory or on firmware storage) an array that stores the parameter values that are computed (e.g., per blocks 1102-1128 of FIG. 11) for the TX electrodes of the sensor array.

Referring to FIG. 12, in block 1132 the processing logic performs an operation that initializes to zero a variable ("txIndex"), which denotes the TX index value of the current TX electrode for which computations are being performed.

In block 1134, the processing logic determines whether there are any remaining TX electrodes which need to be processed. For example, the processing logic performs a comparison operation to compare the value stored in the "txIndex" variable to a variable or constant ("txLast"), which denotes the total number of TX electrodes that need to be processed for tail-effect adjustment (e.g., such as the total number of TX electrodes in the sensor array). If the "txIndex" variable is less than the "txLast" variable, then at least the current TX electrode still needs to be processed, and the processing logic continues to perform the operations in blocks 1136A to 1144. If the "txIndex" variable is not less than the "txLast" variable, then the diff signal values for the sensor elements of all TX electrodes have been processed, and the processing logic proceeds with the operations in block 1250.

In block 1136A, the processing logic performs an operation that initializes to zero a variable ("rxIndex"), which denotes the RX index value of the current RX electrode (along the current TX electrode) for which computations are being performed.

In block 1138, the processing logic determines whether there are any remaining RX electrodes that need to be processed for the current TX electrode. For example, the processing logic performs a comparison operation to compare the value stored in the "rxIndex" variable to a variable or constant ("rxLast"), which denotes the total number of RX electrodes that need to be processed for the current TX electrode. If the "rxIndex" variable is less than the "rxLast" variable, then at least the current RX electrode still needs to be processed and the processing logic continues to perform the operations in blocks 1140 and 1142. If the "rxIndex" variable is not less than the "rxLast" variable, then the diff signal values from the RX electrodes along the current TX electrode have been processed, and the processing logic continues to perform the operation in block 1144 (which sets the next TX electrode for processing).

In block 1140, the processing logic adjusts the diff signal value of the current sensor element (which is formed by the current RX electrode indicated by the "rxIndex" variable and the current TX electrode indicated by the "txIndex" variable) for tail effect. For example, the processing logic may perform the following operation $$\text{Signal}_{corrected} = \text{Signal} - \text{Coef}[txIndex] * rxIndex$$

where "Signal$_{corrected}$" is a variable that stores the diff signal value of the current sensor element as adjusted for tail effect, "Signal" is a variable that stores the measured/obtained diff signal value of the current sensor element that is being processed, and "Coef[txIndex]" is a variable that stores the slope parameter value a that has been computed and stored for the current TX electrode. It is noted that the value (i.e., multiplication product) "Coef[txIndex]*rxIndex" represents the adjustment value that corrects the tail effect for the current sensor element.

In block 1142, the processing logic sets the RX index value of the next RX electrode that needs to be processed and continues with the operation in block 1138. For example, the processing logic performs the operation $$rxIndex++$$

which adds "1" to the "rxIndex" variable in order to indicate that the next RX electrode now becomes the current RX electrode for processing; thereafter, the processing logic continues with the operation in block 1138.

After the diff signal values from all RX electrodes along the current TX electrode have been processed, in block 1138 the processing logic determines that the current "rxIndex" variable is not less than the "rxLast" variable. Thus, the processing logic continues with the operations in block 1144.

In block 1144, the processing logic sets the TX index value of the next TX electrode that needs to be processed and continues with the operation in block 1134. For example, the processing logic performs the operation $$txIndex++$$

which adds "1" to the "txIndex" variable in order to indicate that the next TX electrode now becomes the current TX electrode for processing; thereafter, the processing logic continues with the operation in block 1134.

After the diff signal values for the sensor elements of all TX electrodes have been adjusted in the above manner, in block 1134 the processing logic determines that the current "txIndex" variable is not less than the "txLast" variable. Thus, the processing logic continues with the operations in block 1250.

In block 1250, the processing logic performs the operations described for block 1150 in FIG. 11 (e.g., such as using the tail-effect-corrected signal values to calculate the location position of the conductive object on the sensor array).

Examples of Additional Features and Alternative Embodiments

In some embodiments, the techniques for correcting tail effect described herein may provide for avoiding some of the downsides that may be caused by signal disparity in some operational situations.

For example, in the case of poor grounding the signal under a large conductive object (e.g., such as a fat finger) may have a dip that makes sort of a "donut" contact area. When detected on a sensor array, such "donut"-shaped contact may cause some interior sensor elements to be considered as having a tail effect (e.g., as having diff signal values below the tail-effect threshold) while in fact they are under the contact. In other words, these diff signal values can be low enough to be under the tail-effect threshold that is used in the best fit linear approximation. Thus, when the tail effect correction is applied as described heretofore, the dip ("donut" hole) in the signal values caused by the large conductive object will become larger and may increase the likelihood of contact area separation due to the subtraction of tail-effect adjustments from already low diff signal values. However, such contact area separation is generally undesirable since it may cause the detection (and position calculation) of two separate contacts instead of the actual single contact by the large conductive object (e.g., such as the fat finger).

To address this downside, in some embodiments the techniques described herein provide for correcting the tail effect of only those sensor elements that are downstream from the sensor element having the maximum RX index value. (It is noted that in this context, downstream refers to the direction away from the sensor array edge from which the RX electrodes are routed.)

Figure 13:
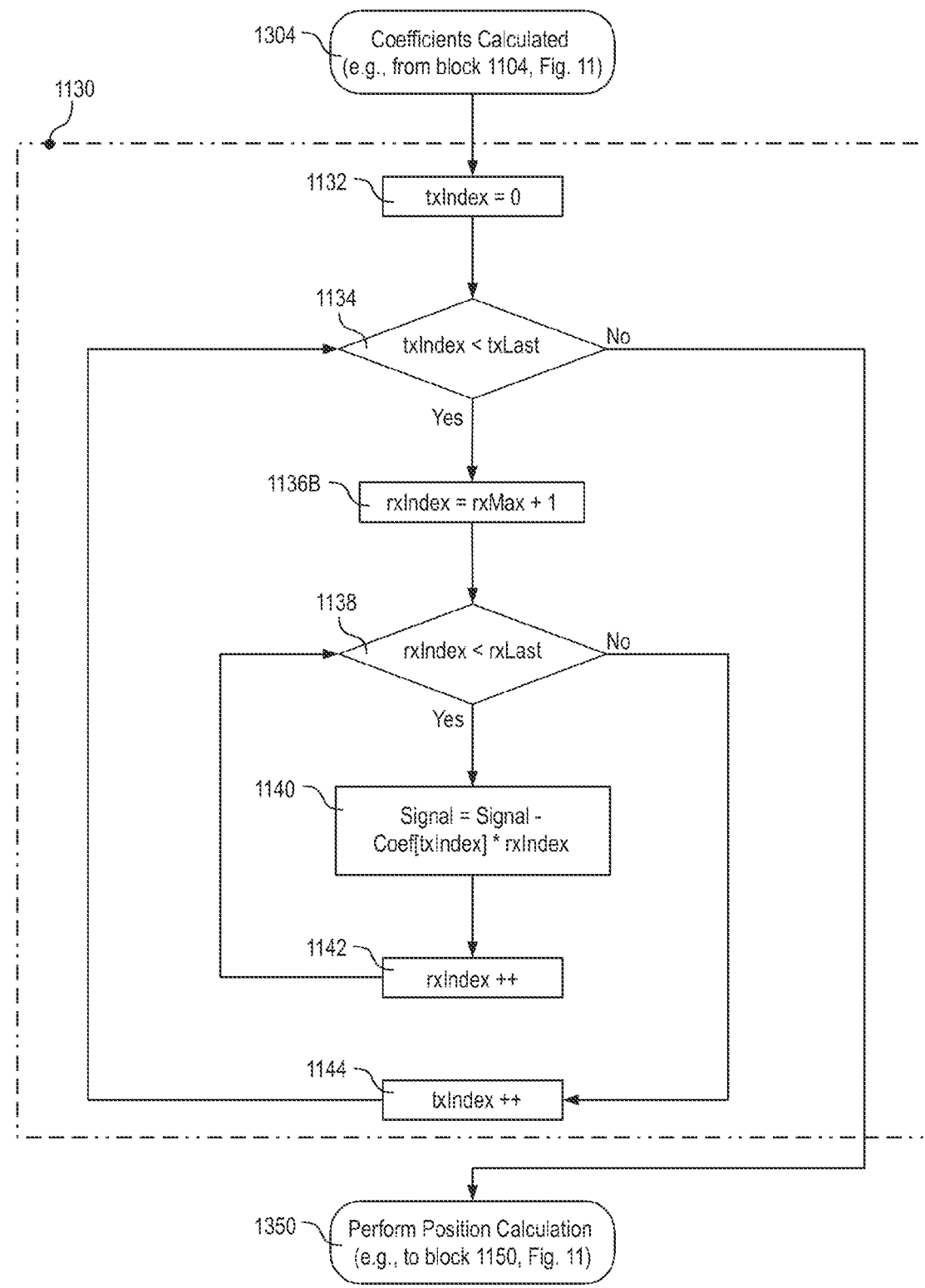
FIG. 13 illustrates an example method of correcting tail effect according to some embodiments that account for contacts by a large conductive object (e.g., such as a fat finger).

FIG. 13 illustrates an example method of adjusting for tail effect that accounts for contacts by a large conductive object (e.g., such as a fat finger) and avoids contact area separation. The method in FIG. 13 includes the same blocks as the method in FIG. 12, except for block 1136B in which different sensor elements are selected as compared to block 1136A in FIG. 12.

The operations in the blocks of FIG. 13 are described hereinafter as being performed by a processing logic (e.g., such as processing logic 102 in FIG. 1). It is noted, however, that various implementations and embodiments may use different, and possibly multiple, components to perform the method of FIG. 13. Thus, the description hereinafter, of the method in FIG. 13 as being performed by a processing logic, is to be regarded in an illustrative rather than a restrictive sense.

At block 1304, the slope parameter (or coefficient) values a for the TX electrodes of the sensor array have already been computed and stored in association with their corresponding TX electrodes. In block 1132 the processing logic performs an operation that initializes to zero the "txIndex" variable that denotes the TX index value of the current TX electrode. In block 1134, the processing logic determines whether there are any remaining TX electrodes which need to be processed. For example, if the "txIndex" variable is less than the "txLast" variable, then at least the current TX electrode still needs to be processed and the processing logic continues to perform the operations in blocks 1136B to 1144. If the "txIndex" variable is not less than the "txLast" variable, then the diff signal values for the sensor elements of all TX electrodes have been processed, and the processing logic proceeds with the operations in block 1350.

In block 1136B, the processing logic selects for tail-effect adjustment only those sensor elements whose RX electrodes are downstream from the RX electrode that detected the maximum diff signal value as part of the scan operation being processed. For example, the processing logic initializes the "rxIndex" variable to a value that is higher than the value of a variable ("rxMax"), which denotes the RX index value of the RX electrode that detected the highest diff signal value along the current TX electrode. To perform this initialization, the processing logic may perform the following operation $$rxIndex = rxMax + 1$$

For the purposes of the above operation, the "rxMax" variable for each TX electrode can be found and saved in association therewith during the linear approximation coefficient calculation (e.g., as part of the operations in blocks 1112 to 1124 in FIG. 11). By setting the "rxIndex" variable in this manner, the techniques described herein provide that diff signal values will be corrected only for those sensor elements whose RX index values are outside of the "rxMax" index values for all TX electrodes. If the sensor array is double-routed, then the operations in block 1136B can be applied separately for each side of the sensor array from which RX electrodes are routed.

In block 1138, the processing logic determines whether there are any remaining RX electrodes that need to be processed for the current TX electrode. For example, if the "rxIndex" variable is less than the "rxLast" variable, then at least the current RX electrode still needs to be processed and the processing logic continues to perform the operations in blocks 1140 and 1142. If the "rxIndex" variable is not less than the "rxLast" variable, then the diff signal values from the RX electrodes along the current TX electrode have been processed, and the processing logic continues to perform the operation in block 1144 (which sets the next TX electrode for processing).

In block 1140, the processing logic adjusts the diff signal value of the current sensor element (which is formed by the current RX electrode indicated by the "rxIndex" variable and the current TX electrode indicated by the "txIndex" variable) for tail effect. For example, the processing logic may perform the following operation $$Signal_{corrected} = Signal - Coef[txIndex] * rxIndex$$

It is noted that the value (i.e., multiplication product) "Coef[txIndex]*rxIndex" represents the adjustment value that corrects the tail effect for the current sensor element.

In block 1142, the processing logic sets the RX index value of the next RX electrode that needs to be processed and continues with the operation in block 1138. After the diff signal values from the selected RX electrodes along the current TX electrode have been processed, in block 1138 the processing logic determines that the current "rxIndex" variable is not less than the "rxLast" variable. Thus, the processing logic continues with the operations in block 1144. In block 1144, the processing logic sets the TX index value of the next TX electrode that needs to be processed and continues with the operation in block 1134. After the diff signal values for the sensor elements of all TX electrodes have been adjusted in the above manner, in block 1134 the processing logic determines that the current "txIndex" variable is not less than the "txLast" variable. Thus, the processing logic continues with the operations in block 1350. In block 1350, the processing logic performs the operations described for block 1150 in FIG. 11 (e.g., such as the operations that use the tail-effect-corrected signal values to calculate the location position of the conductive object on the sensor array).

In some embodiments, a simple (e.g., faster) implementation of the techniques described herein may involve the computation of slope parameter values only for those TX electrodes that are in the middle of the contact area, and the adjustment for tail effect of only those sensor elements that are formed by those TX electrodes. In these embodiments, the methods for correcting tail effect would be similar to the methods illustrated in FIGS. 11 and 12, except that instead of looping through all of the TX electrodes these methods would provide for operations that select only a subset of the TX electrodes (e.g., such as the subset including only those TX electrodes that are in the middle of the contact area).

In some embodiments, the techniques for correcting tail effect described herein may be used not only for mutual capacitance sensor arrays, but also for sensor arrays that have self-capacitance designs. Such application of the techniques described herein would be possible for self-capacitance sensor arrays because they also provide multiple sensors that can be activated and that can produce a signal profile that can be analyzed. Further, the techniques described herein are not tied to capacitive sensing applications only, but can be used with other sensing technologies (e.g., to remove shadows in optical sensing applications) and for any other types of designs that provide an array of sensor elements that can receive a parasitic signal coupling with linear profile.

Various embodiments of the techniques for correcting tail effect described herein may include various operations. These operations may be performed by hardware components, software, firmware, or a combination thereof. As used herein, the term "coupled to" may mean coupled directly or indirectly through one or more intervening components. Any of the signals provided over various buses described herein may be time multiplexed with other signals and provided over one or more common buses. Additionally, the interconnection between circuit components or blocks may be shown as buses or as single signal lines. Each of the buses may alternatively be one or more single signal lines and each of the single signal lines may alternatively be buses.

Certain embodiments may be implemented as a computer program product that may include instructions stored on a non-transitory computer-readable medium, e.g., such as volatile storage and/or non-volatile storage. These instructions may be used to program one or more devices that include one or more general-purpose or special-purpose processors (e.g., such as Central Processing Units, or CPUs) or equivalents thereof (e.g., such as processing cores, processing engines, microcontrollers, and the like), so that when executed by the processor(s) or the equivalents thereof, the instructions cause the device(s) to perform the described operations for correcting tail effect described herein. A computer-readable medium may also include one or more mechanisms for storing or transmitting information in a form (e.g., software, processing application) that is readable by a machine (e.g., such as a device or a computer). The non-transitory computer-readable storage medium may include, but is not limited to, electromagnetic storage medium (e.g., floppy disks, hard disks, and the like), optical storage medium (e.g., CD-ROM), magneto-optical storage medium, read-only memory (ROM), random-access memory (RAM), erasable programmable memory (e.g., EPROM and EEPROM), flash memory, or another now-known or later-developed type of medium that is suitable for storing information.

Although the operations of the method(s) herein are shown and described in a particular order, the order of the operations of each method may be altered so that certain operations may be performed in an inverse order or so that certain operation may be performed, at least in part, concurrently with other operations. In other embodiments, instructions or sub-operations of distinct operations may be in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method of performing a scan operation for a single-layer sensor array comprising transmit (TX) electrodes and receive (RX) electrodes, the method comprising a set of operations, including:
   (a) determining, by a processing device, whether to include a signal value for an RX electrode in a computation of a slope parameter value for a TX electrode;
   (b) computing, by the processing device, an index sum based on an index of the RX electrode when the signal value for the RX electrode is included in the computation of the slope parameter value for the TX electrode;
   (c) computing, by the processing device, a signal sum based on the signal value for the RX electrode when the signal value for the RX electrode is included in the computation of the slope parameter value for the TX electrode; and
   (d) computing, by the processing device, the slope parameter value for the TX electrode based on the signal sum and the index sum.

2. The method of claim 1, further comprising, prior to performing operation (d), repeating operations (a), (b), and (c) for each RX electrode that is interleaved with the TX electrode in the sensor array.

3. The method of claim 1, wherein operation (a) comprises comparing the signal value for the RX electrode to a tail-effect threshold.

4. The method of claim 3, wherein operation (a) further comprises determining to include the signal value for the RX electrode in the computation of the slope parameter value for the TX electrode when the signal value is greater than zero and less than the tail-effect threshold.

5. The method of claim 1, wherein the set of operations further includes:
   (e) using, by the processing device, the slope parameter value to determine an adjustment value corresponding to tail effect for a sensor element, in the sensor array, that is formed by the TX electrode and the RX electrode.

6. The method of claim 5, wherein operation (e) comprises computing the adjustment value for the sensor element by multiplying the slope parameter value and the index of the RX electrode.

7. The method of claim 5, further comprising repeating operation (e) for RX electrodes that form sensor elements with the TX electrode.

8. The method of claim 5, wherein the set of operations further includes:
(f) computing, by the processing device, a corrected signal value for the sensor element based on the adjustment value and the signal value for the RX electrode.

9. The method of claim 8, further comprising repeating operation (f) for RX electrodes that form sensor elements with the TX electrode.

10. The method of claim 8, wherein the set of operations further includes:
(g) calculating, by the processing device, a location position of a conductive object on the sensor array based at least on the corrected signal value for the sensor element.

11. A non-transitory computer-readable medium storing a set of instructions for performing a scan operation for a single-layer sensor array comprising transmit (TX) electrodes and receive (RX) electrodes, the set of instructions including instructions which, when executed by a processing device, cause the processing device to perform operations comprising:
(a) determining whether to include a signal value for an RX electrode in a computation
of a slope parameter value for a TX electrode;
(b) computing an index sum based on an index of the RX electrode when the signal value for the RX electrode is included in the computation of the slope parameter value for the TX electrode;
(c) computing a signal sum based on the signal value for the RX electrode when the signal value for the RX electrode is included in the computation of the slope parameter value for the TX electrode; and
(d) computing the slope parameter value for the TX electrode based on the signal sum and the index sum.

12. The non-transitory computer-readable medium of claim 11, wherein the set of instructions further comprises instructions which, when executed by the processing device, cause the processing device, prior to performing operation (d), to repeat operations (a), (b), and (c) for each RX electrode that is interleaved with the TX electrode in the sensor array.

13. The non-transitory computer-readable medium of claim 11, wherein the instructions that cause operation (a) comprise instructions which, when executed by the processing device, cause the processing device to compare the signal value for the RX electrode to a tail-effect threshold.

14. The non-transitory computer-readable medium of claim 13, wherein the instructions that cause operation (a) further comprise instructions which, when executed by the processing device, cause the processing device to determine to include the signal value for the RX electrode in the computation of the slope parameter value for the TX electrode when the signal value is greater than zero and less than the tail-effect threshold.

15. The non-transitory computer-readable medium of claim 11, wherein the set of instructions further comprises instructions which, when executed by the processing device, cause the processing device to perform an operation of:
(e) using the slope parameter value to determine an adjustment value corresponding to tail effect for a sensor element, in the sensor array, that is formed by the TX electrode and the RX electrode.

16. The non-transitory computer-readable medium of claim 15, wherein the instructions that cause operation (e) comprise instructions which, when executed by the processing device, cause the processing device to compute the adjustment value for the sensor element by multiplying the slope parameter value to the index of the RX electrode.

17. The non-transitory computer-readable medium of claim 15, wherein the set of instructions further comprises instructions which, when executed by the processing device, cause the processing device to repeat operation (e) for RX electrodes that form sensor elements with the TX electrode.

18. The non-transitory computer-readable medium of claim 15, wherein the set of instructions further comprises instructions which, when executed by the processing device, cause the processing device to perform an operation of:
(f) computing a corrected signal value for the sensor element based on the adjustment value and the signal value for the RX electrode.

19. The non-transitory computer-readable medium of claim 18, wherein the set of instructions further comprises instructions which, when executed by the processing device, cause the processing device to repeat operation (f) for RX electrodes that form sensor elements with the TX electrode.

20. The non-transitory computer-readable medium of claim 18, wherein the set of instructions further comprises instructions which, when executed by the processing device, cause the processing device to perform an operation of:
(g) calculating a location position of a conductive object on the sensor array based at least on the corrected signal value for the sensor element.

* * * * *